United States Patent [19]

Ebetino et al.

[11] Patent Number: 5,753,634
[45] Date of Patent: May 19, 1998

[54] QUATERNARY NITROGEN CONTAINING PHOSPHONATE COMPOUNDS, PHARMACEUTICAL COMPOSTIONS, AND METHODS FOR TREATING ABNORMAL CALCIUM AND PHOSPHATE METABOLISM

[75] Inventors: Frank Hallock Ebetino; Marion David Francis, both of Cincinnati, Ohio; Susan Mary Kaas, Sherburne, N.Y.

[73] Assignee: The Procter & Gamble Company, Cincinnati, Ohio

[21] Appl. No.: 52,694

[22] Filed: Apr. 30, 1993

Related U.S. Application Data

[63] Continuation-in-part of Ser. No. 891,487, May 29, 1992, abandoned.

[51] Int. Cl.$^6$ .................... A61K 31/675; A61K 31/66
[52] U.S. Cl. ................. 514/81; 514/91; 514/109; 546/23; 548/111; 562/21
[58] Field of Search .................. 546/23; 514/80, 514/82, 91, 109; 548/111; 562/21

[56] References Cited

U.S. PATENT DOCUMENTS

| | | | |
|---|---|---|---|
| 4,208,401 | 6/1980 | Bauman | 424/54 |
| 4,267,108 | 5/1981 | Blum et al. | 260/326.61 |
| 4,407,761 | 10/1983 | Blum et al. | 260/502.5 C |
| 4,687,768 | 8/1987 | Benedict et al. | 514/102 |
| 4,746,654 | 5/1988 | Breliere et al. | 514/108 |
| 4,784,993 | 11/1988 | Bosies et al. | 514/93 |
| 4,868,164 | 9/1989 | Ebetino et al. | 514/80 |
| 4,876,247 | 10/1989 | Barbier et al. | 514/89 |
| 4,902,695 | 2/1990 | Ornstein | 514/307 |
| 4,922,007 | 5/1990 | Kieczykowski et al. | 562/13 |
| 4,933,472 | 6/1990 | Isomura et al. | 549/218 |
| 4,939,130 | 7/1990 | Jaeggi et al. | 514/94 |
| 4,939,131 | 7/1990 | Benedict et al. | 514/102 |
| 4,971,958 | 11/1990 | Bosies et al. | 514/89 |
| 4,997,821 | 3/1991 | Cordi et al. | 514/82 |
| 5,071,840 | 12/1991 | Ebetino et al. | 514/89 |
| 5,104,863 | 4/1992 | Benedict et al. | 514/80 |
| 5,137,880 | 8/1992 | Ebetino et al. | 514/80 |
| 5,177,240 | 1/1993 | Cordi et al. | 546/23 |

FOREIGN PATENT DOCUMENTS

| | | |
|---|---|---|
| 26738/88 | 6/1989 | Australia . |
| 45467/89 | 5/1990 | Australia . |
| 0100718 | 2/1984 | European Pat. Off. . |
| 0170228 | 2/1986 | European Pat. Off. . |
| 0186405 | 7/1986 | European Pat. Off. . |
| 0298553 | 1/1989 | European Pat. Off. . |
| 4011777 | 10/1990 | Germany . |
| WO 90/12017 | 10/1990 | WIPO . |
| WO 91/10646 | 7/1991 | WIPO . |

Primary Examiner—Amelia Owens
Attorney, Agent, or Firm—Richard A. Hake; Karen F. Clark; William J. Winter

[57] ABSTRACT

Disclosed are quaternary nitrogen-containing, saturated or unsaturated monocyclic and bicyclic ring-containing bisphosphonate compounds, and pharmaceutically-acceptable salts and esters thereof. These compounds, which are useful for treating or preventing disorders of calcium and phosphate metabolism, have the following general structure:

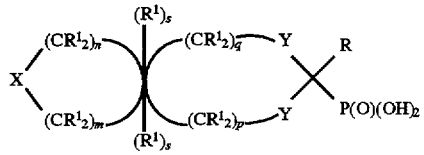

wherein (a) each X and Y are independently selected from nil, O, S, $NR^1$ and $N^+(R^2)_2$; if no $R^1$ is $N^+(R^2)_2$, then at least one of X or Y must be $N^+(R^2)_2$;

(b) m and n and m+n are integers from 0 to 5; p and q and p+q are integers from 0 to 3;

(c) s is an integer from 0 to 2 and when m+n=0 and X is nil, s=2;

(d) each $R^1$ is independently selected from the group consisting of nil, $N^+(R^2)_2$, $R^9SR^6$, $SR^6$, hydrogen, hydroxy; unsubstituted or substituted $C_1$–$C_8$ alkyl, —$OR^3$, —$CO_2R^3$, —$O_2CR^3$, $NR^3_2$, —$N(R^3)C(O)R^3$, —$C(O)N(R^3)_2$, halogen, —$C(O)R^3$, arylalkyl, nitro, unsubstituted or substituted aryl, —OH and combinations thereof;

(e) each $R^2$ is independently selected from the group consisting of nil; substituted or unsubstituted $C_1$–$C_{35}$ alkyl, substituted or unsubstituted phenyl, benzyl, or $R^9SR^6$;

(f) each $R^3$ is independently selected from the group consisting of hydrogen, substituted or unsubstituted $C_1$–$C_8$ alkyl, and $R^9SR^6$;

(g) each $R^6$ is independently selected from the group consisting of H, —$C(O)R^7$, $C(O)OR^7$, $C(S)OR^7$, $C(S)R^7$, $C(O)NR^7_2$, and $C(S)NR^7_2$, wherein $R^7$ is hydrogen or substituted or unsubstituted $C_1$–$C_8$ alkyl;

(h) R is $PO_3H_2$ or $P(O)(OH)R_4$, wherein $R_4$ is substituted or unsubstituted $C_1$–$C_8$ alkyl; and (i) $R^9$ is substituted or unsubstituted C1–C8 alkyl.

22 Claims, No Drawings

QUATERNARY NITROGEN CONTAINING PHOSPHONATE COMPOUNDS, PHARMACEUTICAL COMPOSTIONS, AND METHODS FOR TREATING ABNORMAL CALCIUM AND PHOSPHATE METABOLISM

This application is a CIP of 7/891,487, filed May 29, 1992 now abandoned.

BACKGROUND OF THE INVENTION

This invention relates to novel quaternary nitrogen containing phosphonate compounds. This invention further relates to pharmaceutical compositions containing these novel compounds, as well as to a method of treating or preventing metabolic bone disorders characterized by abnormal calcium and phosphate metabolism by utilizing a compound or pharmaceutical composition of the present invention. Specifically, this invention relates to a method of treating or preventing osteoporosis, and arthritis, especially rheumatoid arthritis and osteoarthritis by utilizing a compound or pharmaceutical composition of the present invention.

A number of pathological conditions which can afflict humans and warm blooded animals involve abnormal calcium and phosphate metabolism. Such conditions may be divided into two broad categories:

(1) Conditions which are characterized by anomalous mobilization of calcium and phosphate leading to general or specific bone loss, such as osteoporosis and Paget's disease, or excessively high calcium and phosphate levels in the fluids of the body, such as hypercalcemia of tumor origin. Such conditions are sometimes referred to herein as pathological hard tissue demineralizations.

(2) Conditions which cause or result from deposition of calcium and phosphate anomalously in the body, such as arthritis, including rheumatoid arthritis and osteoarthritis. These conditions are sometimes referred to herein as pathological calcifications.

The first category includes the most common metabolic bone disorder, osteoporosis; osteoporosis is a condition in which bone hard tissue is lost disproportionately to the development of new hard tissue. Osteoporosis can be generally defined as the reduction in the quantity of bone, or the atrophy of skeletal tissue. Marrow and bone spaces become larger, fibrous binding decreases, and compact bone becomes fragile. Osteoporosis can be subclassified as menopausal, senile, drug-induced (e.g. adrenocorticoid, as can occur in steroid therapy); disease-induced (arthritic and tumor), etc.; however, the manifestations are essentially the same.

In general, there are two types of osteoporosis: primary and secondary. "Secondary osteoporosis" is the result of a separate disease process or agent. However, approximately 90% of all osteoporosis cases are "primary osteoporosis". Such primary osteoporosis includes postmenopausal osteoporosis, disuse osteoporosis age-associated osteoporosis (affecting a majority of individuals over the age of 70 to 80), and idiopathic osteoporosis affecting middle-aged and younger men and women.

For some osteoporotic individuals, the loss of bone tissue is sufficiently great so as to cause mechanical failure of the bone structure. Bone fractures often occur, for example, in the hip and spine of women suffering from postmenopausal osteoporosis. Kyphosis (abnormally increased curvature of the thoracic spine) may also result.

The mechanism of bone loss in osteoporotics is believed to involve an imbalance in the process of "bone remodeling". Bone remodeling occurs throughout life, renewing the skeleton and maintaining the strength of bone. This remodeling involves the erosion and filling of discrete sites on the surface of bones, by an organized group of cells called "basic multicellular units" or "BMUs". BMUs primarily consist of "osteoclasts", "osteoblasts", and their cellular precursors. In the remodeling cycle, bone is resorbed at the site of an "activated" BMU by an osteoclast, forming a resorption cavity. This cavity is then filled with bone by an osteoblast.

Normally, in adults, the remodeling cycle results in a small deficit in bone, due to incomplete filling of the resorption cavity. Thus, even in healthy adults, age-related bone loss occurs. However, in osteoporotics, there may be an increase in the number of BMUs that are activated. This increased activation accelerates bone remodeling, resulting in abnormally high bone loss.

Although its etiology is not fully understood, there are many risk factors thought to be associated with osteoporosis. These include low body weight, low calcium intake, physical inactivity, and estrogen deficiency.

Current osteoporosis treatment consists primarily of calcium and estrogen administration.

The second category, involving conditions manifested by anomalous calcium and phosphate deposition, includes myositis ossificans progressiva, calcinosis universalis, and such afflictions as arthritis (including, for example, rheumatoid arthritis and osteoarthritis), neuritis, bursitis, tendonitis, and other conditions which predispose involved tissue to deposition of calcium.

In addition to osteoporosis, bone loss can result from arthritis, including rheumatoid arthritis and osteoarthritis. Rheumatoid arthritis is a chronic, systemic and articular inflammatory disorder characterized by weakening of the joint capsules and ligaments, followed by destruction of cartilage, ligaments, tendon and bone, and a decrease in viscosity and other alterations in the synovial fluid. Rheumatoid arthritis symptoms include systemic weakness, fatigue, localized pain, stiffness and weakness and swelling and deformation of the joints of the body. Rheumatoid arthritis is most common in women in the fourth to sixth decade of life.

The pathogenesis of rheumatoid arthritis, leading to the destruction of the joints, is characterized by two phases: 1) an exudative phase involving the microcirculation and the synovial cells that allow an influx of plasma proteins and cellular elements into the joint and 2) a chronic inflammatory phase occurring in the sub-synovium and sub-chondral bone, characterized by pannus (granulation tissue) formation in the joint space, bone erosion, and cartilage destruction. The pannus may form adhesions and scar tissue which causes the joint deformities characteristic of rheumatoid arthritis.

The etiology of rheumatoid arthritis remains obscure. Infectious agents such as bacteria and viruses have been implicated. A current hypothesis is that the Epstein-Barr (EBV) virus is a causative agent for rheumatoid arthritis.

Current rheumatoid arthritis treatment consists predominantly of symptomatic relief by administration of non-steroidal anti-inflammatory drugs. Non-steroidal anti-inflammatory drug treatment is mainly effective in the early stages of rheumatoid arthritis; it is unlikely it will produce suppression of joint inflammation if the disease is present for more than one year. Gold, methotrexate, immunosuppressants and corticosteroids have been tried with limited success.

On the other hand, osteoarthritis is an inherently non-inflammatory disorder of the movable joints characterized by deterioration and abrasion of articular cartilage, as well as by formation of new bone at the joint surface. As osteoarthritis progresses, the surface of the articular cartilage is disrupted and wear particles gain access to the synovial fluid which in turn stimulates phagocytosis by macrophage cells. Thus, an inflammatory response is eventually induced in osteoarthritis. Common clinical symptoms of osteoarthritis include cartilaginous and bony enlargements of the finger joints and stiffness on awakening and painful movement.

Common symptomatic treatments for osteoarthritis include analgesics, anti-inflammatories, steroids, and physical therapy.

A variety of polyphosphonic acid derivatives have been proposed for use in the treatment and prophylaxis of diseases involving abnormal calcium and phosphate metabolism. For example, numerous references all incorporated by reference herein, disclose compositions containing polyphosphonates, in particular disphosphonates, such as ethane-1-hydroxy-1,1-diphosphonic acid ("EHDP"), and their use in inhibiting anomalous deposition and mobilization of calcium and phosphate in animal tissue: U.S. Pat. No. 3,683,080, issued Aug. 8, 1972 and U.S. Pat. No. 4,230,700, issued Oct. 28, 1980, both to Francis, and U.S. Pat. No. 4,868,164 to Ebetino, issued Sep. 19, 1989. Numerous other references describe substituted phosphonic acids useful for the treatment of osteoporosis and/or arthritis, and are hereby incorporated by reference herein: U.S. Pat. No. 5,071,840 to Ebetino, et al., issued Dec. 10, 1991, U.S. Pat. No. 4,868, 164, to Ebetino, et al., issued Sep. 19, 1989; U.S. Pat. No. 5,104,863, to Benedict, et al., issued Apr. 14, 1992; U.S. Pat. No. 4,267,108, to Blum et al., issued May 12, 1981; U.S. Pat. No. to Breliere, et al., issued May 24, 1988; U.S. Pat. No. 4,876,247 to Barbier, et al., issued Oct. 24, 1989; European Patent Application Publication No. 100,718, of Breliere S. A., published Feb. 15, 1984; European Patent Application Publication No. 170,228, of Boehringer Mannheim GmbH, published Feb. 5, 1986; European Patent Application Publication No. 186,405, of Benedict and Perkins, published Jul. 2, 1986; European Patent Application Publication No. 298,553, of Ebetino, published Jan. 11, 1989; U.S. Pat. No. 4,754,993, to Bosies, et al., issued Nov. 15, 1988; U.S. Pat. No. 4,939,130 to Jaeggi, et al., issued Jul. 3, 1990; U.S. Pat. No. 4,971,958 to Bosies, et al., issued Nov. 20, 1990; WO 90/12017 to Dunn, et al., published Oct. 18, 1990; WO 91/10646 to Youssefyeh, R., et al., published Jul. 25, 1991; AU-A-26738/88 to Jaeggi, K. A., publication date Jun. 15, 1989; AU-A-45467/89 of Ciba-Geigy, publication date May 31, 1990.

Finally, U.S. Pat. No. 4,208,401, Bauman (assigned to Colgate-Palmolive Co.), issued Jun. 17, 1980 (U.S. '401) discloses non-heterocyclic ring substituted quaternary ammonium bisphosphonates useful as anti-calculus agents.

DE 40 11 777, Jaeggi, K., disclosed Oct. 18, 1990 (DE '777) discloses a heterocyclic ring substituted diphosphonate wherein said heterocyclic ring can be lower alkyl substituted. Said heterocyclic ring is bridged to the phosphonic acid group via a quaternary non-ring nitrogen atom. DE '777 also discloses that the compounds produce pronounced inhibition of bone resorption and thus are useful in treating osteoporosis, inflammatory and degenerative joint diseases, peridontitis, and hyperparathyroidism. The disclosures of these references are incorporated by reference herein.

None of these references, however, disclose the utility of a quaternized-nitrogen-containing cyclic phosphonate compound, useful in preventing and treating both osteoporosis and rheumatoid arthritis and osteoarthritis.

The compounds of the present invention have osteoprotective activity at the site of joint destruction in arthritic conditions and have that activity as an additional benefit in the treatment of arthritis over the above merely relieving the symptoms of inflammation. The term "osteoprotective activity" as used herein means disease-modifying activity on bone and surrounding soft tissue at the site of joint destruction.

It has been surprisingly discovered that the compounds of the present invention, wherein the cyclic phosphonate compound contains a nitrogen atom that is quaternized, have more potent bone antiresorptive activity and therapeutic utility in treating osteoporosis and arthritis, than nitrogen-containing bone active compounds where the nitrogen is not quaternized. Moreover, the compounds of the present invention exhibit unusual solubility properties. Thus, the compounds of the present invention may be more readily orally absorbed. The more readily absorbed a compound, the more effective it may be at lower doses. Lower doses are generally preferable because undesirable side effects are decreased.

It is therefore an object of the present invention to provide new more potent, compounds which are potent bone resorption inhibiting agents useful in osteoporosis therapy and anti-arthritic agents useful in the treatment of arthritis, especially osteoarthritis and rheumatoid arthritis. It is a further object of the present invention to provide pharmaceutical compositions useful for the treatment and prophylaxis of abnormal calcium and phosphate metabolism. In addition, it is an object of the present invention to provide methods for treating or preventing diseases characterized by abnormal calcium and phosphate metabolism in humans or other mammals.

These and other objects of the present invention will become apparent from the detailed disclosure of the present invention provided hereinafter.

SUMMARY OF THE INVENTION

The present invention relates to a quaternary nitrogen containing, saturated or unsaturated monocyclic and bicyclic ring containing phosphonates and the pharmaceutically-acceptable salts and esters thereof, having the following structure:

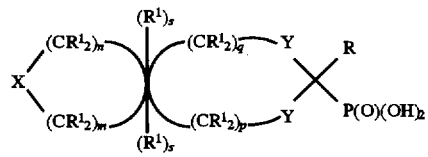

wherein (a) each X and Y are independently selected from nil, O, S, $NR^1$; and $N^+(R^2)_2$; if no $R^1$ is $N^+(R^2)_3$, then at least one of X or Y must be $N^+(R^2)_2$;

(b) m and n and m+n are integers from 0 to 5; p and q and p+q are integers from 0 to 3;

(c) s is an integer from 0 to 2; and when m+n=0 and X is nil, s=2;

(d) each $R^1$ is independently selected from the group consisting of nil, $N^+(R^2)_3$, $R^9SR^6$, $SR^6$, hydrogen, hydroxy; unsubstituted or substituted $C_1$–$C_8$ alkyl, —$OR^3$, —$CO_2R^3$, —$O_2CR^3$, $NR^3_2$, —$N(R^3)C(O)R^3$, —$C(O)N(R^3)_2$, halogen, —$C(O)R^3$ arylalkyl, nitro, unsubstituted or substituted aryl, and combinations thereof;

(e) each $R^2$ is independently selected from the group consisting of nil; a substituted or unsubstituted $C_1$–$C_{35}$ alkyl, substituted or unsubstituted phenyl, benzyl, or $R^9SR^6$;

(f) each $R^3$ is independently selected from the group consisting of hydrogen, substituted or unsubstituted $C_1$–$C_8$ alkyl, and $R^9SR^6$.

(g) each $R^6$ is independently selected from the group consisting of H, —C(O)$R^7$, C(O)O$R^7$, C(S)O$R^7$, C(S)$R^7$, C(O)N$R^7{}_2$; C(S)N$R^7{}_2$, wherein $R^7$ is hydrogen, or substituted or unsubstituted $C_1$–$C_8$ alkyl;

(h) R is COOH, SO$_3$H$_2$, PO$_3$H$_2$, or P(O)(OH)R$_4$, wherein R$_4$ is substituted or unsubstituted $C_1$–$C_8$ alkyl; and (i) $R^9$ is substituted or unsubstituted $C_1$–$C_8$ alkyl.

The present invention further relates to pharmaceutical compositions containing a safe and effective amount of a compound of the present invention, and pharmaceutically-acceptable excipients. Finally, the present invention relates to methods for treating or preventing pathological conditions characterized by abnormal calcium and phosphate metabolism in humans or other mammals. This method comprises administering to a human or other mammal in need of such treatment of a safe and effective amount of a compound or composition of the present invention.

Definitions and Usage of Terms

The following is a list of definitions for terms used herein.

"Heteroatom" is a nitrogen, sulfur, or oxygen atom. Groups containing one or more heteroatoms may contain different heteroatoms.

"Alkyl" is an unsubstituted or substituted, straight-chain or branched, saturated or unsaturated hydrocarbon chain, said hydrocarbon chain may be saturated, having 1 to 8 carbon atoms, and preferably, unless otherwise stated, from 1 to 4 carbon atoms; said hydrocarbon chain may be unsaturated, having 2 to 8 carbon atoms, and preferably, unless otherwise stated, 2 to 4 carbon atoms. Accordingly, the term "alkyl", as used herein, encompasses alkenyl hydrocarbon unsaturated chains having at least one olefinic double bond and alkynyl hydrocarbon unsaturated chains having at least one triple bond. Preferred alkyl groups include, but are not limited to, methyl, ethyl, propyl, isopropyl, and butyl.

"Heteroalkyl" is an unsubstituted or substituted, saturated chain having from 3 to 8-members and comprising carbon atoms and one or two heteroatoms.

"Carbocyclic ring" or "Carbocycle" as used herein is an unsubstituted or substituted, saturated, unsaturated or aromatic, hydrocarbon ring. Carbocycles may be monocyclic or polycyclic: Monocyclic rings generally contain from 3 to 8 atoms, preferably 5 to 7 atoms. Polycyclic rings containing two rings contain 6–16, preferably 10 to 12, atoms and those with three rings generally contain 13 to 17, preferably 14 to 15, atoms.

"Heterocyclic ring" or "Heterocycle" as used herein is an unsubstituted or substituted, saturated, unsaturated or aromatic ring comprised of carbon atoms and one or more heteroatoms in the ring. Heterocyclic rings may be mono- cyclic or polycyclic. Monocyclic rings generally contain from 3 to 8 atoms, preferably 5 to 7 atoms. Polycyclic ring systems consisting of two rings generally contain 6 to 16, preferably from 10 to 12 atoms. Polycyclic ring systems consisting of three rings generally contain 13 to 17 atoms, preferably 14 to 15 atoms. Each heterocyclic ring must have at least one nitrogen atom. Unless otherwise stated the heteroatoms may be independently chosen from nitrogen, sulfur, and oxygen.

"Aryl" is an aromatic carbocyclic ring. Preferred aryl groups include, but are not limited to, phenyl, tolyl, xylyl, cumenyl, and naphthyl.

"Heteroaryl" is an aromatic heterocyclic ring. Preferred heteroaryl groups include, but are not limited to, thienyl, furyl, pyrrolyl, pyridinyl, pyrazinyl, oxazolyl, thiazolyl, quinolinyl, pyrimidinyl, and tetrazolyl.

"Alkoxy" is an oxygen atom having a hydrocarbon chain substituent, where the hydrocarbon chain is an alkyl or alkenyl (e.g., —O-alkyl or —O-alkenyl). Preferred alkoxy groups include, but are not limited to, methoxy, ethoxy, propoxy, and alkyloxy.

"Hydroxyalkyl" is a substituted hydrocarbon chain which has a hydroxy substituent (e.g., —OH), and may have other substituents. Preferred hydroxyalkyl groups include, but are not limited to, hydroxyethyl and hydroxypropyl.

"Carboxyalkyl" is a substituted hydrocarbon chain which has a carboxy substituent (e.g. —COOH) and may have other substituents. Preferred carboxyalkyl groups include carboxymethyl, carboxyethyl, and their acids and esters.

"Aminoalkyl" is a hydrocarbon chain (e.g. alkyl) substituted with an amine moiety (e.g., NH-alkyl—), such as aminomethyl alkyl.

"Alkylamino" is an amino moiety having one or two alkyl substituents (e.g., —N-alkyl), such as dimethylamino.

"Alkenylamino" is an amino moiety having one or two alkenyl substituents (e.g., —N-alkenyl).

"Alkynalamino" is an amino moiety having one or two alkynyl substituents (e.g., —N-alkynyl).

"Alkylimino" is an imino moiety having one or two alkyl substituents (e.g., —N-alkyl—).

"Arylalkyl" is an alkyl moiety substituted with an aryl group. Preferred arylalkyl groups include benzyl and phenylethyl.

"Arylamino" is an amine moiety substituted with an aryl group (e.g., —NH-aryl).

"Aryloxy" is an oxygen atom having an aryl substituent (e.g., —O-aryl).

"Acyl" or "carbonyl" is a carbon to oxygen double bond, e.g. R—C(=O). Preferred acyl groups include, but are not limited to, acetyl, propionyl, butanoyl and benzoyl.

"Acyloxy" is an oxygen atom having an acyl substituent (e.g., —O-acyl); for example, —O—C(=O)-alkyl.

"Acylamino" is an amino moiety having an acyl substituent (e.g., —N-acyl); for example, —NH—(C=O)-alkyl.

"Halo", "halogen", or "halide" is a chloro, bromo, fluoro, or iodo atom radical. Chloro, bromo, and fluoro are preferred halides.

Also, as referred to herein, a "lower" hydrocarbon moiety (e.g., "lower" alkyl) is a hydrocarbon chain comprised of from, unless otherwise stated, 1 to 6, preferably from 1 to 4, carbon atoms.

As used herein the term thio-substituent" (S$R^6$ or $R^9SR^6$) includes thiols [—SH] where $R^6$=H; thioesters [—SC(O)$R^7$] where $R^6$=C(O)$R^7$; dithioesters [—SC(S)$R^7$] where $R^6$=C(S)$R^7$; thiocarbamates [—SC(O)N($R^7$)$_2$] where $R^6$=C(O)N($R^7$)$_2$; dithiocarbamates [—SC(S)N($R^7$)$_2$] where $R^6$=C(S)N($R^7$)$_2$; thiocarbonates [—SC(O)O$R^7$] where $R^6$=C(O)O$R^7$; and dithiocarbonates [—SC(S)O$R^7$] where $R^6$=C(S)O$R^7$. $R^7$ is a hydrogen or $C_1$–$C_8$ alkyl. Any of the S$R^6$ substituents may themselves be substituted with an $R^9$ moiety, where $R^9$ is a substituted or unsubstituted $C_1$–$C_8$ alkyl. Accordingly, additional thio-substituents denoted by $R^9SR^6$ are alkylthiols, alkylthioesters, alkyldithioesters, alkylthiocarbamates, alkyldithiocarbamates, alkylthiocarbonates and alkyl dithiocarbonates.

The term "bisphosphonate" and "bisphosphonic acid" as used herein relate to those phosphonate or phosphonic acids that have two phosphonate groups attached to the same carbon atom and are used interchangeably with the terms "diphosphonate" and "diphosphonic acids." Using the structures described here, the moiety R is $PO_3H_2$.

A "pharmaceutically-acceptable" salt is a cationic salt formed at any acidic (e.g., carboxyl) group, or an anionic salt formed at any basic (e.g., amino) group. Many such salts are known in the art, as described in World Patent Publication 87/05297, Johnston et al., published Sep. 11, 1987, hereby incorporated by reference herein. Preferred cationic salts include the alkali-metal salts (such as sodium and potassium), and alkaline earth metal salts (such as magnesium and calcium). Preferred anionic salts include the halides (such as chloride), acetate and phosphate salts.

A "biohydrolyzable ester" is an ester of the quaternary nitrogen containing bicyclic containing compounds that does not interfere with the therapeutic activity of the compounds, or that is readily metabolized by a human or other mammal. Many such esters are known in the art, as described in World Patent Publication 87/05297, Johnston et al., published Sep. 11, 1987, and hereby incorporated by reference herein. Such esters include lower alkyl esters, lower acyloxyalkyl esters (such as acetoxylmethyl, acetoxyethyl, aminocarbonyloxymethyl, pivaloyloxymethyl, and pivaloyloxyethyl esters), lactonyl esters (such as phthalidyl and thiophthalidyl esters), lower alkoxyacyloxyalkyl esters (such as methoxycarbonyloxymethyl, ethoxycarbonyloxyethyl and isopropoxycarbonyloxyethyl esters), alkoxyalkyl esters, choline esters, and acylamino alkyl esters (such as acetamidomethyl esters).

As defined above and as used herein, substituent groups may themselves be substituted. Such substitution may be with one or more substituents. Such substituents include, but are not limited to, those listed in C. Hansch and A. Leo, *Substituent Constants for Correlation Analysis in Chemistry and Biology* (1979), hereby incorporated by reference herein. Preferred substituents include, but are not limited to, alkyl, alkenyl, alkoxy, hydroxy, oxo, amino, aminoalkyl (e.g. aminomethyl, etc.), cyano, halo, carboxy, alkoxyacetyl (e.g. carboethoxy, etc.), thio, thiol, aryl, cycloalkyl, heteroaryl, heterocycloalkyl (e.g., piperidinyl, morpholinyl, piperazinyl, pyrrolidinyl, etc.), imino, thioxo, hydroxyalkyl, aryloxy, arylalkyl, and combinations thereof.

DETAILED DESCRIPTION OF THE INVENTION

Quaternary Nitrogen-Containing Phosphonate Compounds

The compounds of the present invention are cyclic ring containing phosphonates, and the pharmaceutically-acceptable salts and esters thereof, which are substituted at the phosphonic acid containing carbon with a phosphonic acid group, rendering a bisphosphonate compound; or with a carboxylic acid group, rendering a phosphonocarboxylate compound; or with a sulfonic acid group, rendering a phosphonosulfonate compound; or with a phosphinic acid group, rendering a phosphonoalkylphosphinate compound. Preferred phosphonate compounds described herein are bisphosphonates or phosphonoalkylphosphinates. Said phosphonate compounds may be monocyclic or polycyclic, carbocyclic or heterocyclic rings wherein the phosphonic acid carbon is a member of the ring structure. This quaternary nitrogen-containing cyclic phosphonate compound has the general structure:

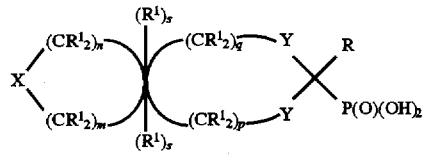

wherein m and n and m+n are integers from 0 to 5 (preferred is m+n=3, and most preferred is m=0 and n=3); p and q are integers from 0 to 3; p+q=3; s is an integer from 0 to 2 and when m+n=0 and X is nil; s=2. Each X and Y are independently chosen from $N^+(R^2)_2$, nil, O, S or $NR^1$. Each $R^1$ is independently selected from the group consisting of nil, $N^+(R^2)_3$, $R^9SR^6$, $SR^6$, hydrogen, hydroxy, unsubstituted or substituted $C_1-C_8$ alkyl, $-OR^3$, $-CO_2R_3$, $-O_2CR_3$, $-NR^3_2$, $-N(R^3)C(O)R^3$, $-C(O)N(R^3)_2$, halogen, $C(O)R^3$, arylalkyl, nitro, unsubstituted or substituted aryl, and combinations thereof; each $R^2$ is independently selected from nil, a substituted or unsubstituted alkyl from 1–35 carbons, a substituted or unsubstituted phenyl, benzyl, or $R^9SR^6$; each $R^3$ is independently selected from the group consisting of hydrogen, substituted or unsubstituted $C_1-C_8$ alkyl (preferred $R^3$ are hydrogen, methyl, and ethyl); and $R^9SR^6$ where $R^6$ is independently selected from the group consisting of H, $-C(O)R^7$, $-C(S)R^7$, $-C(O)NR^7_2$; $-C(S)NR^7_2$, $-C(O)OR^7$, $-C(S)OR^7$, wherein $R^7$ is hydrogen or substituted or unsubstituted $C_1-C_8$ alkyl. $R^9$ is substituted or unsubstituted $C_1-C_8$ alkyl. R is independently selected from COOH, $SO_3H$, $PO_3H_2$ and $P(O)(OH)(R_4)$ wherein $R_4$ is an $C_1-C_8$ alkyl.

Preferred $R^1$ is $N^+(R^2)_3$, nil, $R^9SR^6$, $SR^6$, hydrogen, unsubstituted or substituted $C_1-C_8$ alkyl, $-NR^3_2$, and hydroxy; preferred $R^2$ is substituted or unsubstituted alkyl having from 1 to 35 carbon atoms, or $R^9SR^6$. More preferred $R^1$ is hydrogen, $SR^6$, methyl, ethyl, $-NH_2$, and hydroxy; and most preferred $R^1$ is SH. More preferred $R^2$ is methyl and ethyl; and most preferred $R^2$ is methyl.

As stated above, if no $R^1$ is $N^+(R^2)_3$, then at least one of X or Y must be $N^+(R^2)_2$.

Preferred compounds of the present invention are substituted or unsubstituted octahydro diphosphonopyrindinium, and the pharmaceutically-acceptable salts and esters thereof, having the general structures:

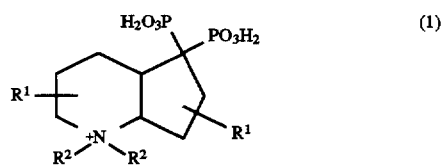

(1)

referred to herein as "unsubstituted or substituted octahydro-5,5-diphosphono-1,1-dialkyl-1-pyrindinium";

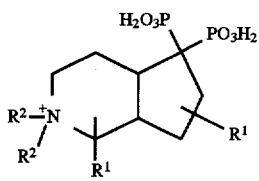
(2)

referred to herein as "unsubstituted or substituted octahydro-5,5-diphosphono-2,2-dialkyl-2-pyrindinium salts";

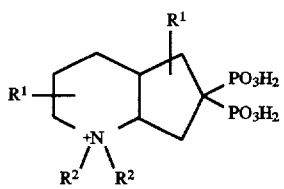
(3)

referred to herein as "unsubstituted or substituted octahydro-6,6-diphosphono-1,1-dialkyl-1-pyrindinium salts";

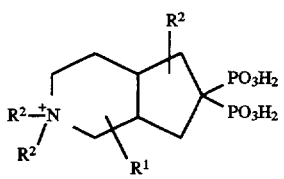
(4)

referred to herein as "unsubstituted or substituted octahydro-6,6-diphosphono-2,2-dialkyl-2-pyrindinium salts";

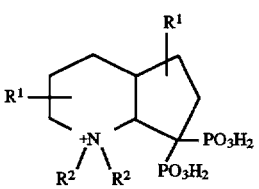
(5)

referred to herein as "octahydro-7,7-diphosphono-1,1-dialkyl-1-pyrindinium salts";

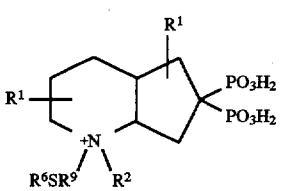
(6)

referred to herein as "octahydro-6,6-diphosphono-1-alkyl-1-thioalkyl-1-pyrindinium salts";

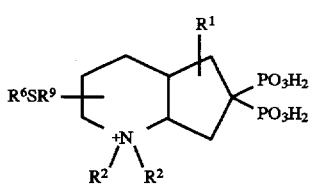
(7)

referred to herein as thio-substituted "octahydro-6,6-diphosphono-1,1-dialkyl-1-pyrindinium salts"; and

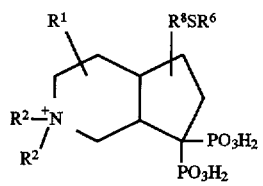
(8)

referred to herein as "a thio-substituted octahydro-7,7-diphosphono-2,2-dialkyl-2-pyrindinium salts".

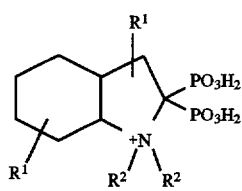
(9)

referred to herein as a "2,2-diphosphonoindolinium salt".

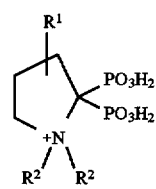
(10)

referred to herein as a "2,2-diphosphonopyrrolidinium salt".

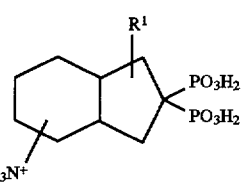
(11)

referred to herein as a "diphosphonoammonium salt".

More preferred compounds of the present invention are substituted or unsubstituted octahydro-6,6-diphosphono-1,1-dialkyl-1-pyrindinium salts, and the pharmaceutically-acceptable salts and esters thereof; and substituted or unsubstituted octahydro-6,6-diphosphono-2,2-dialkyl-2-pyrindinium salts, octahydro-6,6-diphosphono-1-alkyl-1-thioalkyl-1-pyrindinium salts, and the pharmaceutically-acceptable salts and esters thereof. Most preferred compounds of the present invention are substituted or unsubstituted octahydro-6,6-diphosphono-1,1-dialkyl-1-pyrindinium salts and octahydro-6,6-diphosphono-1-alkyl-1-thioalkyl-1-pyrindinium salts, and the pharmaceutically-acceptable salts and esters thereof.

Specific examples of compounds of the present invention are:

octahydro-1,1-dimethyl-5,5-diphosphono-1-pyrindinium salt;
octahydro-2,2-dimethyl-5,5-diphosphono-2-pyrindinium salt;
octahydro-1,1-dimethyl-6,6-diphosphono-1-pyrindinium salt;
octahydro-2,2-methyl-6,6-diphosphono-2-pyrindinium salt;
octahydro-1,1-dimethyl-7,7-diphosphono-1-pyrindinium salt;
octahydro-2,2-dimethyl-7,7-diphosphono-2-pyrindinium salt;
octahydro-5,5-diphosphono-1,1,2-trimethyl-1-pyrindinium salt;
octahydro-1,3-diethyl-2,2-dimethyl-5,5-diphosphono-2-pyrindinium salt;

octahydro-1,1-dimethyl-6,6-diphosphono-7-hydroxy-1-pyrindinium salt;
octahydro-2,2-dimethyl-6,6-diphosphono-4-methoxy-2-pyrindinium salt;
octahydro-7,7-diphosphono-1-ethyl-1-methyl-5-vinyl-1-pyrindinium salt;
octahydro-2,2-dimethyl-1-(dimethylamino)-7,7-diphosphono-2-pyrindinium salt;
octahydro-2-(3,4-dichlorophenyl)-1,1-dimethyl-7,7-diphosphono-1-pyrindinium salt;
octahydro-1,1-diethyl-2-(p-dimethylaminophenyl)-7,7-diphosphono-1-pyrindinium salt;
octahydro-4-chloro-1,1-diethyl-6,6-diphosphono-1-pyrindinium salt;
octahydro-4-amino-6,6-diphosphono-1-ethyl-1-propyl-1-pyrindinium salt;
octahydro-7-carboxy-6,6-diphosphono-1,1-dipropyl-1-pyrindinium salt;
octahydro-5-carboxymethylester)-1,1-dimethyl-6,6-diphosphono-1-pyrindinium salt;
octahydro-2,2-diethyl-6,6-diphosphono-4-hydroxy-2-pyrindinium salt;
octahydro-5,5-diphosphono-2-ethyl-7-(ethylketone)-2-methyl-2-pyrindinium salt;
octahydro-1,1-dimethyl-6,6-diphosphono-4-nitro-1-pyrindinium salt;
octahydro-1,1-dimethyl-5,5-diphosphono-1-pyrindinium salt;
octahydro-2,2-dimethyl-5,5-diphosphono-2-pyrindinium salt;
octahydro-1,1-dimethyl-6,6-diphosphono-1-pyrindinium salt;
octahydro-2,2-methyl-6,6-diphosphono-2-pyrindinium salt;
octahydro-1,1-dimethyl-7,7-diphosphono-1-pyrindinium salt;
octahydro-2,2-dimethyl-7,7-diphosphono-2-pyrindinium salt;
octahydro-6,6-diphosphono-1,1,2-trimethyl-1-pyrindinium salt; and
octahydro-4-amino-1,1-dimethyl-6,6-diphosphono-1-pyrindinium salt;
and the pharmaceutically-acceptable salts and esters thereof. The most preferred compounds of the present invention are octahydro-6,6-diphosphono-1-alkyl-1-thioalkyl-1-pyrindinium salt and octahydro-6,6-diphosphono-1,1-dialkyl-1-pyrindinium salt, and the pharmaceutically-acceptable salts and esters thereof.

It is further desirable that the bicyclic compounds of the present invention have a "cis" ring juncture. Therefore, it is preferred, for example, that octahydro-6,6-diphosphono-1,1-dialkyl-1-pyrindinium salt have the structure:

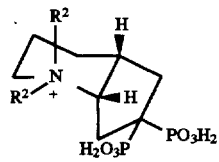

The term "pharmaceutically-acceptable salts and esters", as used herein, means hydrolyzable esters and salts of the diphosphonate compounds which have the same general pharmacological properties as the acid form from which they are derived, and which are acceptable from a toxicity viewpoint. Pharmaceutically acceptable salts include alkali metals (e.g., sodium and potassium), alkaline earth metals (e.g., calcium and magnesium), non-toxic heavy metals (e.g., stanous and indium), and ammonium and low molecular weight substituted ammonium (e.g., mono-, di- and triethanolamine) salts. Preferred compounds are the sodium, potassium, and ammonium salts.

The compounds of the present invention have demonstrated significantly better bone anti-resorptive activity than art-known diphosphonate compounds such as ethane-1-hydroxy-1,1-diphosphonic acid ("EHDP"; disclosed in U.S. Pat. No. 3,683,080 to Francis, issued Aug. 8, 1972) and azacyclopentane-2,2-diphosphonic acid (disclosed in U.S. Pat. No. 3,988,443 to Ploger et al., issued Oct. 26, 1976). More surprisingly, the compounds of the present invention have demonstrated significantly better bone anti-resorptive activity than compounds which have very similar chemical structures. For example, octahydro-6,6-diphosphono-1,1-dimethyl-1-pyrindinium chloride of the present invention surprisingly is a much more potent bone resorption inhibiting agent than the following chemically very similar compounds (disclosed in European Patent Application Publication No. 189,662):

1) dihydro-1-pyrindine-6,6-diphosphonate, having the structure:

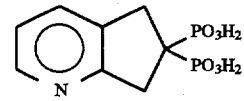

2) hexahydroindan-2,2-diphosphonate, having the structure:

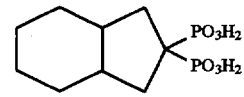

3) indan-2,2-diphosphonate, having the structure:

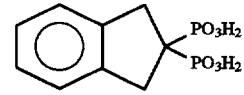

In addition, the compounds of the present invention have demonstrated very low toxicity, and therefore are believed to have very good therapeutic indices. Finally, at an effective dose for inhibition of bone resorption, the compounds of the present invention are expected to inhibit bone mineralization either very little or not at all.

In order to determine and assess pharmacological activity, testing of the quaternary cyclic phosphonate compounds in animals is carried out using various assays known to those skilled in the art. Thus, the in vivo bone antiresorptive activity may be conveniently demonstrated using an assay designed to test the ability of these compounds to inhibit the resorption of bone, which bone resorption is characteristic of abnormal calcium and phosphate metabolism. One such test known to those skilled in the art is the Schenk model. Another useful art-known test is the adjuvant arthritis test. Also useful is the in vitro hydroxyapatite crystal growth inhibition test. These and other appropriate tests for pharmacological activity are disclosed and/or referred to in Shinoda et al., *Calcified Tissue International*, 35, pp 87–99 (1983); Schenk et al., *Calcified Tissue Research*, 11, pp 196–214 (1973); Russell et al., *Calcified Tissue Research*, 6, pp 183–196 (1970); Muhlbauer and Fleisch, *Mineral Electrolyte Metab.*, 5, pp 296–303 (1981); Nancollas et al., *Oral*

Biol., 15, 731 (1970); U.S. Pat. No. 3,683,080, to Francis, issued Aug. 8, 1972; U.S. Pat. No. 4,134,969, to Schmidt-Dunker, issued Jan. 16, 1979; and EPO Patent Application Publication No. 189,662, published Aug. 6, 1986; the disclosures of all these articles and patent specifications being incorporated herein by reference in their entirety. Certain of these tests for pharmacological activity are also described in more detail in the Examples provided hereinafter.

In addition to being useful for treating or preventing pathological conditions characterized by abnormal calcium or phosphate metabolism, the compounds of the present invention may have other uses. For example, the compounds of the present invention are believed to be useful as bone scanning agents after labeling with 99m-technetium. In addition, the compounds of the present invention are useful as sequestering agents for polyvalent metal ions, particularly di-(e.g. calcium and magnesium) and trivalent (e.g. indium) metal ions. Thus, the compounds of the present invention are useful as builders in detergents and cleansers, or for treating water. They are also useful as stabilizers for compounds. In addition, they may be useful in preventing the formation of tartar (i.e., calculus) and/or plaque on teeth. Finally, the compounds of the present invention may be useful as herbicides which are non-toxic to animals.

The cyclic phosphonate compounds of the present invention are prepared from commercially-available materials according to non-limiting Examples 1 to 14. Generally, the synthesis reaction may be carried out in the following way: In a first step, a methane diphosphonate ester, in solution, is converted to the corresponding carbanion. In a second step, to this reaction mixture is added a solution of hydrocarbon compound suitably activated for a double nucleophilic substitution. A third step is performed through which any unsaturation in the compound is saturated, usually by hydrogenation. Finally, in a fourth step the amine is quaternized by reaction with an alkyl halide.

Typically, a solution of methane diphosphonate ester is added to a cold suspension of potassium hydride in an inert organic solvent, and the solution is left to stir at room temperature. The suitably activated hydrocarbon is then added as a solution to the reaction mixture, and the entire mixture is heated to about 80° C. until completion. After the mixture is cooled, filtered, and concentrated, the concentrate is chromatographed on silica gel to obtain the desired ester. This ester is hydrolyzed by refluxing in HCL and the resulting material concentrated under vacuum. The residue is dissolved in $H_2O$ and treated with activated charcoal. Following filtration, the solution is concentrated, and the product is dried under vacuum. If necessary, the material is hydrogenated in solution over an appropriate catalyst and then purified. Finally, the amine is quaternized by reaction with an alkyl halide such as methyl iodide in a mixture of typically water/ethanol or water/DMSO. Representative procedures for synthesizing compounds of the present invention are provided in the Examples 1 to 13 hereinafter.

Compositions Containing Novel Quaternary Nitrogen Containing Bicyclic Compounds

The novel quaternary nitrogen-containing, cyclic phosphonate compounds of the present invention may be administered to humans or other mammals by a variety of routes, including, but not limited to, oral dosage forms and injections (intravenous, intramuscular, intraperitoneal and subcutaneous). Numerous other dosage forms containing the novel quaternary nitrogen-containing, cyclic phosphonate compounds of the present invention can be readily formulated by one skilled in the art, utilizing the suitable pharmaceutical excipients as defined below. For considerations of patient compliance, oral dosage forms are generally most preferred.

The term "pharmaceutical composition" as used herein means a combination comprised of a safe and effective amount of the quaternary nitrogen-containing cyclic phosphonate compound active ingredient, or mixtures thereof, and pharmaceutically-acceptable excipients.

The phrase "safe and effective amount", as used herein, means an amount of a compound or composition large enough to significantly positively modify the symptoms and/or condition to be treated, but small enough to avoid serious side effects (at a reasonable benefit/risk ratio), within the scope of sound medical judgment. The safe and effective amount of active ingredient for use in the pharmaceutical compositions to be used in the method of the invention herein will vary with the particular condition being treated, the age and physical condition of the patient being treated, the severity of the condition, the duration of the treatment, the nature of concurrent therapy, the particular active ingredient being employed, the particular pharmaceutically-acceptable excipients utilized, and like factors within the knowledge and expertise of the attending physician.

The term "pharmaceutically-acceptable excipients" as used herein includes any physiologically inert, pharmacologically inactive material known to one skilled in the art, which is compatible with the physical and chemical characteristics of the particular quaternary nitrogen-containing phosphonate compound active ingredient selected for use. Pharmaceutically-acceptable excipients include, but are not limited to, polymers, resins, plasticizers, fillers, binders, lubricants, glidants, disintegrants, solvents, co-solvents, buffer systems, surfactants, preservatives, sweetening agents, flavoring agents, pharmaceutical grade dyes or pigments, and viscosity agents.

The term "oral dosage form" as used herein means any pharmaceutical composition intended to be systemically administered to an individual by delivering said composition to the gastrointestinal tract of an individual, via the mouth of said individual. For purposes of the present invention, the delivered form can be in the form of a tablet, coated or non-coated; solution; suspension; or a capsule, coated or non-coated.

The term "injection" as used herein means any pharmaceutical composition intended to be systemically administered to a human or other mammal, via delivery of a solution or emulsion containing the active ingredient, by puncturing the skin of said individual, in order to deliver said solution or emulsion to the circulatory system of the individual either by intravenous, intramuscular, intraperitoneal or subcutaneous injection.

The rate of systemic delivery can be satisfactorily controlled by one skilled in the art, by manipulating any one or more of the following:

(a) the active ingredient proper;

(b) the pharmaceutically-acceptable excipients; so long as the variants do not interfere in the activity of the particular active ingredient selected;

(c) the type of the excipient, and the concomitant desirable thickness and permeability (swelling properties) of said excipients;

(d) the time-dependent conditions of the excipient itself and/or within the excipients;

(e) the particle size of the granulated active ingredient; and (f) the pH-dependent conditions of the excipients.

In particular, the solubility, acidity, and susceptibility to hydrolysis of the different quaternary nitrogen-containing phosphonate active ingredients, such as acid addition salts, salts formed with the carboxylic group, e.g., alkali metal salts, alkaline earth metal salts, etc., and esters, e.g., alkyl, alkenyl, aryl, aralkyl, may be used as guidelines for the proper choice. In addition, suitable pH-conditions might be established within the oral dosage forms by adding a suitable buffer to the active ingredient in accordance with the desired release pattern.

As stated hereinabove, pharmaceutically-acceptable excipients include, but are not limited to, resins, fillers, binders, lubricants, solvents, glidants, disintegrants co-solvents, surfactants, preservatives, sweetener agents, flavoring agents, buffer systems, pharmaceutical-grade dyes or pigments, and viscosity agents.

The preferred solvent is water.

Flavoring agents among those useful herein include those described in *Remington's Pharmaceutical Sciences*, 18th Edition, Mack Publishing Company, 1990, pp. 1288–1300, incorporated by reference herein. The pharmaceutical compositions suitable for use herein generally contain from 0–2% flavoring agents.

Dyes or pigments among those useful herein include those described in *Handbook of Pharmaceutical Excipients*, pp. 81–90, 1986 by the American Pharmaceutical Association & the Pharmaceutical Society of Great Britain, incorporated by reference herein. The pharmaceutical compositions herein generally contain from 0–2% dyes or pigments.

Preferred co-solvents include, but are not limited to, ethanol, glycerin, propylene glycol, polyethylene glycols. The pharmaceutical compositions of the present invention include from 0–50% co-solvents.

Preferred buffer systems include, but are not limited to, acetic, boric, carbonic, phosphoric, succinic, malaic, tartaric, citric, acetic, benzoic, lactic, glyceric, gluconic, glutaric and glutamic acids and their sodium, potassium and ammonium salts. Particularly preferred are phosphoric, tartaric, citric, and acetic acids and salts. The pharmaceutical composition of the present invention generally contain from 0–5% buffer systems.

Preferred surfactants include, but are not limited to, polyoxyethylene sorbitan fatty acid esters, polyoxyethylene monoalkyl ethers, sucrose monoesters and lanolin esters and ethers, alkyl sulfate salts, sodium, potassium, and ammonium salts of fatty acids. The pharmaceutical compositions of the present invention include 0–2% surfactants.

Preferred preservatives include, but are not limited to, phenol, alkyl esters of parahydroxybenzoic acid, o-phenylphenol benzoic acid and the salts thereof, boric acid and the salts thereof, sorbic acid and the salts thereof, chlorobutanol, benzyl alcohol, thimerosal, phenylmercuric acetate and nitrate, nitromersol, benzalkonium chloride, cetylpyridinium chloride, methyl paraben, and propyl paraben. Particularly preferred are the salts of benzoic acid, cetylpyridinium chloride, methyl paraben and propyl paraben. The compositions of the present invention generally include from 0–2% preservatives.

Preferred sweeteners include, but are not limited to, sucrose, glucose, saccharin, sorbitol, mannitol, and aspartame. Particularly preferred are sucrose and saccharin. Pharmaceutical compositions of the present invention include 0–5% sweeteners.

Preferred viscosity agents include, but are not limited to, methylcellulose, sodium carboxymethylcellulose, hydroxypropyl-methylcellulose, hydroxypropylcellulose, sodium alginate, carbomer, povidone, acacia, guar gum, xanthan gum and tragacanth. Particularly preferred are methylcellulose, carbomer, xanthan gum, guar gum, povidone, sodium carboxymethylcellulose, and magnesium aluminum silicate. Compositions of the present invention include 0–5% viscosity agents.

Preferred fillers include, but are not limited to, lactose, mannitol, sorbitol, tribasic calcium phosphate, dibasic calcium phosphate, compressible sugar, starch, calcium sulfate, dextro and microcrystalline cellulose. The compositions of the present invention contain from 0–75% fillers.

Preferred lubricants include, but are not limited to, magnesium stearate, stearic acid, and talc. The pharmaceutical compositions of the present invention include 0.5–2% lubricants.

Preferred glidants include, but are not limited to, talc and colloidal silicon dioxide. The compositions of the present invention include from 1–5% glidants.

Preferred disintegrants include, but are not limited to, starch, sodium starch glycolate, crospovidone, croscarmelose sodium, and microcrystalline cellulose. The pharmaceutical compositions of the present invention include from 4–15% disintegrants.

Preferred binders include, but are not limited to, acacia, tragacanth, hydroxypropylcellulose, pregelatinized starch, gelatin, povidone, hydroxypropylcellulose, hydroxypropylmethylcellulose, methylcellulose, sugar solutions, such as sucrose and sorbitol, and ethylcellulose. The compositions of the present invention include 1–10% binders.

Compounds of the present invention may comprise from about 0.1% to about 99.9% by weight of the pharmaceutical compositions of the present invention. Preferably the compounds of the present invention comprise from about 20% to about 80% by weight of the pharmaceutical compositions of the present invention.

Accordingly, the pharmaceutical compositions of the present invention include from 15–95% of a quaternary nitrogen containing phosphonate compound active ingredient, or mixture, thereof; 0–2% flavoring agents; 0–50% co-solvents; 0–5% buffer system; 0–2% surfactants; 0–2% preservatives; 0–5% sweeteners; 0–5% viscosity agents; 0–75% fillers; 0.5–2% lubricants; 1–5% glidants; 4–15% disintegrants; and 1–10% binders.

Suitable pharmaceutical compositions are described herein in Examples 17–19. It is well within the capabilities of one skilled in the art to vary the non-limiting examples described herein to achieve a broad range of pharmaceutical compositions.

The choice of a pharmaceutically-acceptable excipient to be used in conjunction with the phosphonate compounds of the present invention is basically determined by the way the phosphonate compound is to be administered. If the compound is to be injected, the preferred pharmaceutical carrier is sterile physiological saline, the pH of which has been adjusted to about 7.4. Suitable pharmaceutically-acceptable carriers for topical application include those suited for use in creams, gels, tapes and the like.

The preferred mode of administering the phosphonate compound of the present invention is orally. The preferred unit dosage form is therefore tablets, capsules and the like, comprising a safe and effective amount of the phosphonate compound of the present invention. Preferably, the compositions comprise from about 1 mg P to about 600 mg P of a phosphonate compound of the present invention. Pharmaceutically-acceptable carriers suitable for the preparation of unit dosage forms for oral administration are well known in the art. Their selection will depend on secondary considerations like taste, cost, and shelf stability, which are not critical for the purposes of the present invention, and can be made without difficulty by a person skilled in the art.

The term "mg P", as used herein, means the weight of the phosphorus atoms present in an amount of a phosphonate compound of the present invention. This unit is used to standardize the amount of the diphosphonic acid compounds of the present invention to be used in the pharmaceutical compositions and methods of the present inventions. For example, dihydro-6,6-diphosphono-1-methyl-1-pyrindinium iodide has a molecular weight of 421 g/mole, of which 15% (62 g/mole) is due to the two phosphorus atoms present in this molecule. One milligram of this compound is therefore calculated to have 0.15 mg P. Thus, to prepare a pharmaceutical composition containing 0.15 mg P of this compound, the composition should contain 1 mg of the compound; and to dose 0.15 mg P/kg of this compound to a 50 kg patient, the patient would be dosed with 50 mg of this compound.

The pharmaceutically-acceptable carrier employed in conjunction with the phosphonate compounds of the present invention is used at a concentration sufficient to provide a practical size to dosage relationship. The pharmaceutically-acceptable carriers, in total, may comprise from 0.1% to 99.9% by weight of the pharmaceutical compositions of the present invention, and preferably from 20% to 80%.

Method for Treating or Preventing Diseases Characterized by Abnormal Calcium and Phosphate Metabolism Another aspect of the present invention is methods for treating or preventing diseases characterized by abnormal calcium and phosphate metabolism. Such methods comprise administering to a human or lower animal in need of such treatment a safe and effective amount of a phosphonate compound of the present invention.

The preferred mode of administration is oral, but other known methods of administration are contemplated as well, e.g., dermatomucosally (for example, dermally, rectally and the like) and parenterally (for example, by subcutaneous injection, intramuscular injection, intra-articular injection, intravenous injection and the like). Inhalation is also included. Thus, specific modes of administration include, without limitation, oral, transdermal, mucosal, sublingual, intramuscular, intravenous, intraperitoneal, and subcutaneous administration, as well as topical application.

The term "abnormal calcium and phosphate metabolism", as used herein, means (1) conditions which are characterized by anomalous mobilization of calcium and phosphate leading to general or specific bone loss, or excessively high calcium and phosphate levels in the fluids of the body; and (2) conditions which cause or result from deposition of calcium and phosphate anomalously in the body. The first category includes, but is not limited to, osteoporosis, Paget's disease, hyperparathyroidism, hypercalcemia of malignancy, heterotopic ossification, and osteolytic bone metastases. The second category includes, but is not limited to, myositis ossificans progressiva, calcinosis universalis, and such afflictions as arthritis, osteoarthritis, neuritis, bursitis, tendonitis and other inflammatory conditions which predispose involved tissue to deposition of calcium phosphates.

The term "rheumatoid arthritis" as used herein, means a chronic systemic and articular inflammatory disorder of unknown etiology. It is characterized by destruction of articular cartilage, ligaments, tendons, and bone.

The term "osteoarthritis" as used herein, means a non-inflammatory disorder of the movable joints. It is characterized by deterioration and abrasion of the articular cartilage; and new bone formation at the joint surface.

The terms "person at risk" and "person in need of such treatment", as used herein, mean any human or lower animal which suffers a significant risk of abnormal calcium and phosphate metabolism if left untreated, and any human or lower animal diagnosed as being afflicted with abnormal calcium and phosphate metabolism. For example, postmenopausal women; persons undergoing certain steroid therapy; persons on certain anticonvulsant drugs; persons diagnosed as having Paget's disease, hyperparathyroidism, hypercalcemia of malignancy, or osteolytic bone metastases; persons diagnosed as suffering from one or more of the various forms of osteoporosis; persons belonging to a population group known to have a significantly higher than average chance of developing osteoporosis, e.g., postmenopausal women, men over age 65, and persons being treated with drugs known to cause osteopetrosis as a side effect; persons diagnosed as suffering from myositis ossificans progressiva or calcinosis universalis; and persons afflicted with arthritis, osteoarthritis, neuritis, bursitis, tendonitis and other inflammatory conditions which predispose involved tissue to deposition of calcium phosphate.

The phrase "safe and effective amount", as used herein, means an amount of a compound or composition high enough to significantly positively modify the condition to be treated, but low enough to avoid serious side effects (at a reasonable benefit/risk ratio), within the scope of sound medical judgment. The safe and effective amount of diphosphonate compounds of the present invention will vary with the particular condition being treated, the age and physical condition of the patient being treated, the severity of the condition, the duration of the treatment, the nature of concurrent therapy, the specific diphosphonate employed, the particular pharmaceutically-acceptable carrier utilized, and like factors within the knowledge and expertise of the attending physician. However, single dosages can range from 0.01 mg P to 3500 mg P, or from 0.0002 to 70 mg P/kg of body weight (based on a body weight of 50 kg). Preferred single dosages are from 1 mg P to 600 mg P, or from 0.02 to 12 mg P/kg of body weight (based on a body weight of 50 kg). Up to four single dosages per day may be administered. Daily dosages greater than 500 mg P/kg are not required to produce the desired effect and may produce undesirable side effects. The higher dosages within this range are, of course, required in the case of oral administration because of limited absorption.

The following Examples further describe and demonstrate the preferred embodiments within the scope of the present invention. The Examples are given solely for the purpose of illustration, and are not to be construed as limitations of the present invention since many variations thereof are possible without departing from its spirit and scope.

EXAMPLE 1

Synthesis of Octahydro-6,6-diphosphono-11-dimethyl-1-pyrindinium Iodide

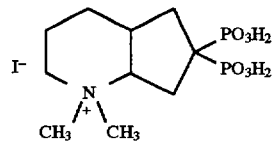

(a) Synthesis of Dihydro-1-pyrindine-6,6-diphosphonic acid:

To an ice bath chilled solution of 35% potassium hydride in mineral oil (5.2 g; 0.045 moles) stirring under argon in 70 ml of DMSO (dry) is added a solution of tetraisopropylmethylenediphosphonate (7.82 g; 0.023 moles) in 30 ml of DMSO. On completion of a dropwise addition, the resulting solution is stirred at room temperature for one hour. A solution of 2,3-bis(chloromethyl) pyridine (4.0 g; 0.023 mole) (crude product as isolated by K. Tsuda et al., *Chem Pharm Bull.*, 1, (1953), 142) in 15 ml of DMSO is slowly added and the reaction mixture is then heated at 90° C. for 1 hour. After cooling, the DMSO is removed under vacuum. 2.1 g of the desired product is purified via flash chromatography using 5–15% ethanol in a methylene chloride gradient on silica gel.

The ester (1.92 g; 0.0043 mole) is added to 38 ml of 6N HCl, and then refluxed with stirring under an argon atmosphere for 18 hours. The resulting precipitate is filtered, rinsed with water (2×5 ml), and dried to yield 0.8 g of an off-white crystalline solid.

(b) Hydrogenation to Octahydro-1-pyrindine-6,6-diphosphonic acid hydrate:

Dihydro-1-pyrindine-6,6-diphosphonic acid (0.86 g, which is prepared as in part (a) hereinbefore), 70 ml of distilled $H_2O$ and $PtO_2$ (0.30 g) are placed in a 500 ml Parr hydrogenation bottle. The mixture is hydrogenated at room temperature (40 psi) for 2 days. The solution is filtered and washed with hot distilled $H_2O$. The filtrate is then concentrated on a rotary evaporator. The resultant solid is then dried under vacuum overnight to give 0.75 g of white crystals, mp 365° C.

(c) Octahydro-1-pyrindine-6,6-bisphosphonic acid, (0.71 g, 2.49 mmol) is dissolved in a mixture of DMSO (10 ml) and water (50 ml). To this is added methyl iodide (5.30 g. 37.35 mmol). The solution is heated at reflux under an atmosphere of nitrogen for 3 days. The reaction mixture is concentrated under reduced pressure and the quaternized product (1.01 g) is obtained by recrystallization from water/isopropanol.

Various substituted octahydro-1-pyrindinium-6,6-diphosphonic acid compounds are prepared as described, hereinbefore, in Example 1, using as the starting material the appropriately substituted 2,3-bis(chloromethyl)pyridine. Such substituted starting materials may be prepared by (1) photochemically reacting substituted 2,3-dimethyl pyridine with N-chlorosuccinimide in $CCl_4$; or (2) esterifying substituted 2,3-dicarboxy pyridine with $MeOH/H^+$, followed by reduction with $LiAlH_4$, and then chlorination with $SOCl_2$. Thus, by analogous synthesis procedures the following compounds are prepared (O-6,6-DP-1-P=octahydro-6,6-diphosphono-1-pyrindinium): 2-methyl-O-6,6-DP-1-P from 6-methyl-2,3-bis(chloromethyl)pyridine; 4-ethyl-2-methyl-O-6,6-DP-1-P from 4-ethyl-6-methyl-2,3-bis(chloromethyl) pyridine; 3-propyl-5-methyl-O-6,6-DP-1-P from 5-propyl-3-(1'-chloroethyl)-2-chloromethyl-pyridine; 4-hydroxy-O-6,6-DP-1-P from 4-hydroxy-2,3-bis(chloromethyl)pyridine; 3-ethoxy-O-6,6-DP-1-P from 5-ethoxy-2,3-bis (chloromethyl)pyridine; 3-carboxy-7-ethyl-O-6,6-DP-1-P from 5-carboxy-3-chloromethyl-2-(1'-chloropropyl) pyridine; 2-phenyl-O-6,6-DP-1-P from 6-phenyl-2,3-bis (chloromethyl)pyridine; 3-(p-methoxybenzyl)-O-6,6-DP-1-P from 5-(p-methoxybenzyl)-2,3-bis(chloromethyl) pyridine; 4-amino-O-6,6-DP-1-P from 4-nitro-2,3-bis (chloromethyl)pyridine; 4-chloro-O-6,6-DP-1-P from 4-chloro-2,3-bis(chloromethyl)pyridine; and 5-carboxy (methyl ester)-O-6,6-DP-1-P from 3-(2'-chloro-2'-acetic acid, methyl ester)-2-chloromethyl-pyridine.

EXAMPLE 2

Synthesis of Octahydro-6,6-dihosphono-2,2-dimethyl-2-pyrindinium Iodide.

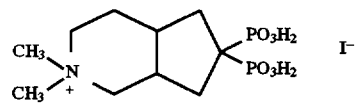

Using essentially the same procedure as in Example 1(a), tetraisopropyl methylene diphosphonate is converted to tetraisopropyl dihydro-2-pyrindine-6,6-diphosphonate by reaction with 3,4-bis(chloromethyl)pyridine. The resulting ester is hydrolyzed as in Example 1(a) to yield dihydro-2-pyrindine-6,6-diphosphonic acid. The dihydro-2-pyrindine-6,6-diphosphonic acid is then converted to the octahydro-2-pyrindine-6,6-diphosphonic acid by a hydrogenation procedure which is essentially the same as in Example 1(b). Substituted octahydro-2-pyrindine-6,6-diphosphonic acid compounds are prepared as described hereinbefore, in Example 1, by using as the starting material the appropriately substituted 3,4-bis(chloromethyl)pyridine.

Using essentially the same procedure as Example 1, octahydro-2-pyrindine-6,6-bisphosphonic acid is converted to octahydro-6,6-diphosphono-2,2-dimethyl-2-pyrindinium iodide.

EXAMPLE 3

Synthesis of Octahydro-7,7-diphosphono-1,1-dimethyl-1-pyrindinium Iodide:

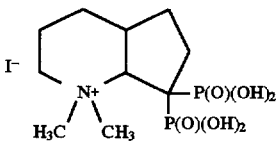

(a) Synthesis of the substituted or unsubstituted octahydro-1-pyrindine-7,7-diphosphonate compounds may be achieved using a synthesis procedure analogous to the procedure for making cyano compounds disclosed in Crossley and Shepherd, *J. Chem. Soc., Perkin Trans.* 1, (11), 2479–81(1985), the disclosure of which is incorporated herein by reference in its entirety. Therefore, to a 0° C. solution of cyclopentenopyridine (1 mmol) in 2 ml of THF (anhydrous) is added a pregenerated 3 ml solution of lithium diisopropyl amide (2 mmol). After stirring for 30 minutes at 0° C. under a nitrogen atmosphere, diethylchlorophosphite in 2 ml of THF is added dropwise. The reaction is stirred for 1 hour at 0° C., and then an additional hour at room temperature. The resulting mixture is quenched with saturated ammonium chloride and extracted with methylene chloride. Drying and concentration of solvent gives the crude product which is chromatographed to purity to yield tetraethyl dihydropyrindine-7,7-diphosphonate. This material is hydrolyzed and then hydrogenated by essentially the same procedures as described hereinbefore to yield octahydro-1-pyrindine-7,7-diphosphonic acid.

(b) Octahydro-1-pyrindine-7,7-diphosphonic acid, prepared as described herein in Example 3(a) above, is dissolved in a mixture of DMSO (10 ml) and water (50 ml). To this is added methyl iodide (5.30 g, 37.35 mmol) and the solution is heated at reflux under an atmosphere of nitrogen for 3 days. The reaction mixture is concentrated under reduced pressure and the quaternized product (1.01 g) is obtained by recrystallization from water/isopropanol.

EXAMPLE 4

Synthesis of Dihydro-6,6-diphosphono-1-methyl-1-pyrindinium Inner Salt, Monosodium Salt

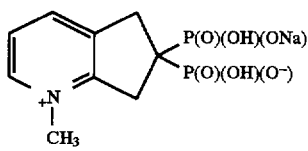

The above compound is prepared and synthesized as described hereinbelow.

Synthesis of Dihydro-6,6-Diphosphono-1-methyl-1-pyridinium Iodide

Dihydro-1-pyrindine-6,6-diphosphonic acid (0.5 g, 1.79 mmol) prepared as described in Example 1a, is dissolved in a solution of water (14 ml) and 1N NaOH (4.5 ml). To this is added methyl iodide (0.56 g, 8.95 mmol) in ethanol (9 ml) and the solution is heated at 80° C. for 18 hours. The pH is monitored over the course of the reaction and base is added as needed to maintain pH 7.0. After heating is complete, the reaction mixture is cooled; then concentrated under reduced pressure. The solid residue is triturated with acetone then recrystallized from water and ethanol.

EXAMPLE 5

Synthesis of Dihydro-6,6-diphosphono-2-methyl-2-pyrindinium Iodide

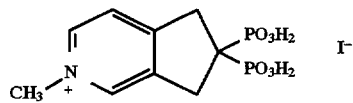

Using essentially the same procedure as in Example 4, dihydro-2-pyrindine-6,6-diphosphonic acid prepared as described in Example 1, is converted to dihydro-6,6-diphosphono-2-methyl-2-pyrindinium iodide.

EXAMPLE 6

Synthesis of Tetrahydro-8,8-diphosphono-1-methylguinolinium Iodide

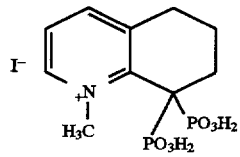

Tetrahydro-8,8-diphosphono-1-methylquinolinium Iodide is prepared and synthesized as described hereinbelow.

I. Synthesis of 5,6,7,8-Tetrahydro-1-quinoline-8,8-bis (phosphonic acid)tetraethyl ester Synthesis of substituted or unsubstituted tetrahydro-1-quinoline-8,8-bisphosphonate compounds may be achieved using a synthesis procedure analogous to the procedure for making cyano compounds disclosed in Crossley and Sheperd, J. Chem. Soc., Perkin Trans. 1, (11), 2479–81 (1985), the disclosure of which is incorporated herein by reference in its entirety. Therefore, to a 0° C. solution of 5,6,7,8-tetrahydroquinoline (1 mmol) in THF (2 ml) is added a pregenerated 3 ml solution of lithium diisopropyl amide (2 mmol). After stirring for 30 minutes at 0° C. under a nitrogen atmosphere, diethylchlorophosphite (2.2 mmol) in THF (2 ml) is added dropwise. The reaction is stirred for 1 hour at 0° C., and then an additional hour at room temperature. The resulting mixture is quenched with saturated aqueous ammonium chloride and extracted with methylene chloride. The combined organic layers are dried over sodium sulfate, filtered and concentrated under reduced pressure. The crude residue is chromatographed to purity to yield tetrahydro-tetraethyl-1-quinoline-8,8-bis(phosphonic acid)tetraethyl ester.

II. Synthesis of 5,6,7,8-Tetrahydro-1-quinoline-8,8-bisphosphonic acid

The tetraethyl ester (5.0 mmol) is added to 6N HCl (38 ml) and stirred at reflux under an atmosphere of nitrogen for 18 hours. The reaction mixture is cooled to room temperature and concentrated under reduced pressure. The resulting crude residue is triturated with acetone and the product is obtained by recrystalizing from water and isopropanol.

III. Synthesis of 5,6,7,8-Tetrahydro-8,8-diphosphono-1-methylquinolinium Iodide

Using essentially the same procedure as in Example 4, 5,6,7,8-tetrahydro-1-quinoline-8,8-bisphosphonic acid is converted to 5,6,7,8-tetrahydro-8,8-diphosphono-1-methylquinolinium iodide.

EXAMPLE 7

Synthesis of Dihydro-7,7-diphosphono-1-methyl-1-pyrindinium iodide

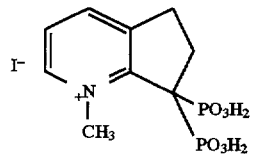

Using essentially the same procedure as in Example 4, dihydro-1-pyrindine-7,7-bisphosphonic acid prepared as described in Example 3, part a, is converted to dihydro-7,7-diphosphono-1-methylpyrindinium iodide.

EXAMPLE 8

Synthesis of Octahydro-8,8-diphosphono-1,1-dimethylquinolinium Iodide

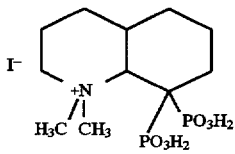

I. Synthesis for Octahydro-1-quinoline-8,8-bisphosphonic acid 5,6,7,8-Tetrahydro-1-quinoline-8,8-bisphosphonic acid (3.0 mmol), which is prepared as in Example 6, part II, water (70 ml) and PtO$_2$ (0.03 g) are placed in a 500 ml Parr hydrogenation bottle. The mixture is hydrogenated at room temperature (40 psi) for 2 days. The solution is filtered and washed with hot water. The resultant solid is dried under vacuum overnight to yield octahydro-1-quinoline-8,8-bisphosphonic acid.

II. Synthesis of octahydro-8,8-diphosphono-1,1-dimethylquinolinium iodide

Using essentially the same procedure as in Example 3, part (b), octahydro-1-quinoline-8,8-bisphosphonic acid is converted to octahydro-8,8-diphosphono-1,1-dimethylquinolinium iodide.

EXAMPLE 9

Dihydro-1-methyl-6-phosphono-6-sulfono-1-pyrindinium Chloride

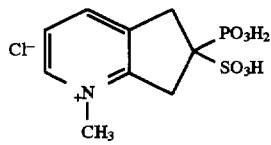

The above compound is prepared and synthesized as described hereinbelow.

I. Synthesis of Dihydro-6-diethoxyphosphinyl-1-pyrindine-6-sulfonic acid, ethyl ester To an ice bath chilled solution of 35% potassium hydride in mineral oil (5.0 mmol) stirring under argon DMSO (7 ml) is added a solution of diethoxyphosphinyl methanesulfonic acid, ethyl ester (2.5 mmol) [prepared as described in J. C. Carretero, et. al., *Tetrahedron*, Vol. 43, pp. 5125–5134 (No. 21) 1987] in DMSO (5 ml). On completion of a dropwise addition, the resulting solution is stirred at room temperature for one hour. A solution of 2,3-bis(chloromethyl)pyridine (2.5 mmol) [prepared as described in K. Tsuda, et. al., *Chem. Pharm. Bull.*, Vol.1, pp. 142, 1953] in DMSO (2 ml) is added slowly and the reaction mixture is then heated at 90° C. for 1 hour. After cooling, the reaction mixture is concentrated under reduced pressure and the desired product is purified by flash chromatography using a 5–15% isopropanol in methylene chloride gradient on silica gel.

II. Synthesis of Dihydro-6-diethoxyphosphinyl-6-ethoxysulfinyl-1-methyl-1-pyrindinium Chloride Dihydro-6-diethoxyphosphinyl-1-pyrindine-6-sulfonic acid, ethyl ester (15 mmol) and iodomethane (45 mmol) in dry acetonitrile (50 ml) are heated at reflux for 48 hours under an atmosphere of nitrogen. Following completion, the reaction mixture is concentrated under reduced pressure and the resulting crude residue is triturated in diethyl ether and the desired product is purified by flash chromatography using a 15% isopropanol in methylene chloride on silica gel.

III. Synthesis of Dihydro-1-methyl-6-phosphono-6-sulfono-1-pyrindinium Chloride

The pyrindinium salt (10 mmol) is heated to reflux in 6N HCl (35 ml) for 24 hours. The reaction mixture is concentrated under reduced pressure and the resulting crude residue is triturated in ethanol. The product is obtained by recrystallizing from water and isopropanol.

EXAMPLE 10

Synthesis of Octahydro-1,1-dimethyl-6-phosphono-6-sulfono-1-pyrindinium Chloride

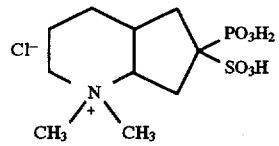

The above compound is prepared and synthesized as described hereinbelow.

I. Synthesis of Octahydro-1-methyl-6-phosphono-6-sulfono-1-pyrindinium Chloride

Dihydro-1-methyl-6-phosphono-6-sulfono-1-pyrindinium chloride (3 mmol) [prepared as described in Example 9 hereinbefore], distilled water (70 ml) and $PtO_2$ (0.30 g) are placed in a 500 ml Parr hydrogenation bottle. The mixture is hydrogenated at room temperature (40 psi) for 2 days. The solution is filtered through celite and washed with hot water. The filtrate is concentrated under reduced pressure and the resultant solid is further dried under vacuum overnight.

II. Synthesis of Octahydro-1,1-dimethyl-6-phosphono-6-sulfono-1-pyrindinium Chloride Octahydro-1-methyl-6-phosphono-6-sulfono-1-pyrindinium chloride (1.8 mmol) is dissolved in a solution of water (15 ml) and brought to pH7 with 1N NaOH. To this is added methyl iodide (9.0 mmol) in ethanol (10 ml) and the solution is heated at 80° C. for 18 hours. The pH is monitored over the course of the reaction and base is added as needed to maintain pH 7.0. After heating is complete, the reaction mixture is cooled then concentrated under reduced pressure. The solid residue is triturated with acetone then recrystallized from water and ethanol.

EXAMPLE 11

Synthesis of Octahydro-6,6-diphosphono-1-(2-mercaptoethyl)-1-methyl-1-pyrindinium chloride

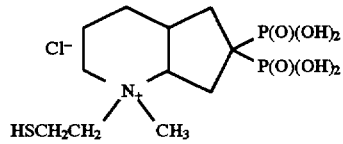

The above compound is prepared and synthesized as described hereinbelow.

I. Synthesis of Octahydro-1-methyl-1-pyrindine-6,6-diphosphonic acid

Dihydro-6,6-diphosphono-1-methyl-1-pyrindinium inner salt, monosodium salt [prepared as described in Example 4 hereinbefore] is hydrogenated using essentially the same procedure as described in Example 1 (part B) hereinbefore to provide octahydro-1-methyl-1-pyrindine-6,6-diphosphonic acid.

II. Synthesis of Octahydro-6,6-diphosphono-1-(2-acetylthioethyl)-1-methyl-1-pyrindinium bromide Octahydro-1-methyl-1-pyrindine-6,6-diphosphonic acid (0.12 mmol) is dissolved in a mixture of water (25 ml) and DMSO (5 ml). To this is added 2-acetylthioethyl bromide (0.60 mmol) and the reaction mixture is heated at 60° for 24 hours. The reaction mixture is cooled, treated with charcoal, filtered and concentrated under reduced pressure. The crude residue is triturated with diethylether and the product can be obtained by recrystallizing the solid residue in water and isopropanol.

III. Synthesis of Octahydro-6,6-diphosphono-1-(2-mercaptoethyl)-1-methyl-1-pyrindinium chloride Octahydro-6,6-diphosphono-1-(2-acetylthioethyl)-1-methyl-1-pyrindinium bromide (0.05 mmol) is heated at reflux in 6N HCl (15 ml) under an atmosphere of nitrogen. The reaction mixture is cooled, treated with charcoal and filtered. The resulting filtrate is concentrated under reduced pressure. The resulting solid residue can be recrystallized from water and ethanol to provide the desired product.

EXAMPLE 12

Synthesis of Octahydro-6,6-diphosphono-1,1-dimethyl-3-(2-mercaptoethyl)-1-pyrindinium iodide

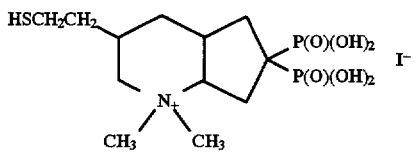

I. Synthesis of Dihydro-3-bromo-1-pyrindine-6,6-diphosphonic acid tetra ethyl ester To an ice chilled solution of 35% potassium hydride in mineral oil (50 mmol) stirring under argon in 70 ml of DMSO (dry) is added a solution of tetraethylmethylenediphosphonic acid (23 mmol) in 30 ml of DMSO. On completion of a dropwise addition, the resulting solution is stirred at room temperature for one hour. A solution of 2,3-bis(chloromethyl)-5-bromo pyridine (23 mmol) [prepared using essentially the same procedure as described on K. Tsuda et al., Chem. Pharm. Bull., 1 (1953) 142] in 15 ml of DMSO is added slowly and the reaction mixture is heated at 90° C. for 1 hour. After cooling, the DMSO is removed under vacuum. The desired product is purified by flash chromatography using 5–15% ethanol in methylene chloride gradient or silica gel.

II. Synthesis of Dihydro-3-(2-hydroxyethyl)-1-pyrindine-6,6-diphosphonic acid tetraethyl ester To a solution of dihydro-3-bromo-1-pyrindine-6,6-diphosphonic acid tetraethylester (10 mmol) in THF (10 ml) cooled to −78° C. is added a solution of n-butyllithium (2.1 equiv) in hexane over 30 minutes. The reaction is kept at −78° C. for an additional 30 minutes. To this solution is added 2-iodoethanol trimethylsilyl (TMS) ether (2.5 equiv) and the reaction is allowed to warm to room temperature over 30 minutes. After standard aqueous work-up, dihydro-3-(2-hydroxyethanol, TMS ether)-1-pyrindine-6,6-diphosphonic acid tetraethyl ester is isolated and used in the subsequent reaction without purification.

Cleavage of the TMS ether from the product is accomplished by stirring it in THF and adding a solution of tetrabutylammonium fluoride (1M in THF) dropwise over 30 minutes. The reaction is quenched by the addition of a saturated aqueous solution of ammonium chloride and the mixture is extracted with methylene chloride. The organic extracts are dried over sodium sulfate, filtered and concentrated under reduced pressure. The resulting oil is used directly in the subsequent reaction.

III. Synthesis of Dihydro-3-(2-acetythioethyl)-1-pyrindine-6,6-diphosphonic acid tetraethyl ester a) A mixture of dihydro-3-(2-hydroxyethyl)-1-pyrindine-6,6-diphosphonic acid tetraethyl ester (10 mmol) carbon tetrabromide (11 mmol) and triphenyl phosphine (11 mmol) in dichloromethane (100 ml) is stirred at room temperature for 5 hours. Water is added and the product is extracted with dichloromethane. The combined organic extracts are dried and concentrated. The residue is purified by flash column chromatography to give dihydro-3-(2-acetylthioethyl)-1-pyrindine-6,6-diphosphonic acid tetraethyl ester.

b) A solution of dihydro-3-(2-acetylthioethyl)-1-pyrindine-6,6-diphosphonic acid tetraethyl ester (5.0 mmol) is stirred in dry acetone (35 ml) and sodium thioacetate (5.2 mmol) is added. The mixture is stirred at 50° C. for 12 hours. After cooling to room temperature the solvent is removed under reduced pressure. The crude residue is dissolved in methylene chloride and washed with water. The organic layer is then dried and concentrated under reduced pressure. The desired product is purified by flash chromatography using a 5–10% isopropanol in methylene chloride gradient on silica gel.

IV. Synthesis of Dihydro-3-(2-mercaptoethyl)-1-pyrindine-6,6-diphosphonic acid

Using essentially the same hydrolysis procedure as described in Example 11, Part III, hereinbefore, dihydro-3-(2-acetylthioethyl)-1-pyrindine-6,6-diphosphonic acid tetraethyl ester is converted to dihydro-3-(2-mercaptoethyl)-1-pyrindine-6,6-diphosphonic acid.

V. Synthesis of Octahydro-3-(2-mercaptoethyl)-1-pyrindine-6,6-diphosphonic acid

Using essentially the same hydrogenation procedure as described in Example 1, part (b), hereinbefore, the dihydro derivative is converted to octahydro-3-(2-mercaptoethyl)-1-pyrindine-6,6-diphosphonic acid.

VI. Synthesis of Octahydro-6,6-diphosphono-1,1-dimethyl-3-(2-mercaptoethyl)-1-pyrindinium iodide Using essentially the same procedure as described in Example 3, part (b), hereinbefore, octahydro-3-(2-mercaptoethyl)-1-pyrindine-6,6-diphosphonic acid is converted to octahydro-6,6-diphosphone-1,1-dimethyl-3-(2-mercaptoethyl)-1-pyrindinium iodide.

EXAMPLE 13

Synthesis of 1,3-dihydro-4-(2-mercaptoethyl)-2,2-diphosphono-2H-pyrrolo[3,2-b]pyridinium chloride

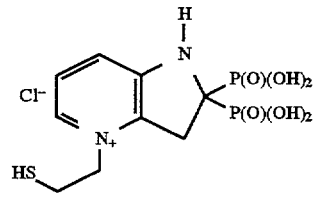

I. Synthesis of 1,3-dihydro-4-(2-acetylthioethyl)-2-oxo-2H-pyrrolo[3,2-b]pyridinium bromide To 1,3-dihydro-2H-pyrrolo[3,2-b]pyridin-2-one (6.25 g, 0.05 mol) [prepared as described in J. Org. Chem. Vol. 37, pp. 51–4, 1972] in acetonitrile (500 ml) is added S-acetyl-2-bromoethanethiol. The reaction mixture is heated at reflux for 12 hours under an atmosphere of nitrogen. The reaction mixture is the concentrated under reduced pressure and the crude residue is triturated in diethyl ether. The product can be further purified by flash chromatography with 5% isopropanol in methylene chloride on silica gel.

II. Synthesis of 1,3-dihydro-4-(2-mercaptoethyl)-2,2-diphosphono-2H-pyrrolo[3,2-b]pyridinium chloride 1,3-Dihydro-4-(2-acetylthioethyl)-2-oxo-2H-pyrrolo[3,2-b]pyridiniumbromide is treated with phosphorous acid (7.7 g) in chlorobenzene (28 ml) and heated to 110° C. To the rapidly stirring mixture is added phosphorus trichloride (9.0 ml) and the heating is continued for 5 hours. After cooling to ambient temperature the solvent is decanted and aqueous HCl (28 ml, 1M) is added. The mixture is heated at reflux for an additional 12 hours. The reaction mixture is cooled and concentrated to dryness. After triturating the residue with several portions of acetone, the bisphosphonic acid is obtained in a pure state.

EXAMPLE 14

Synthesis of 2,2-Diphosphono-1,1-dimethylpyrrolidinium hydroxide, Inner Salt

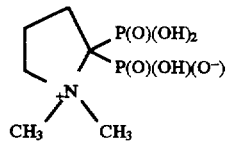

I. Synthesis of pyrrolidine-2,2-bisphosphonic acid

Pyrrolidinone (5 g, 58.7 mmol) is treated with phosphorous acid (14.4 g, 176 mmol) in chlorobenzene (75 ml) and heated to 110° C. To the rapidly stirring mixture is added phosphorus trichloride (15.4 ml, 176 mmol) and the heating is continued for 5 hours. After cooling to ambient temperature the solvent is decanted and aqueous HCl (50 ml, 1M) is added to the crude residue. The mixture is heated at reflux for an additional 12 hours. The reaction mixture is cooled and concentrated to dryness. After triturating the residue with several portions of acetone, the bisphosphonic acid is obtained as a white solid.

II. Synthesis of 2,2-Diphosphono-1,1-dimethylpyrrolidium Inner

Salt Pyrrolidine-2,2-bisphosphonic acid is dissolved in water (10 ml) and ethanol (2 ml) and to this is added an excess of methyl iodide. The reaction mixture is heated at reflux under an atmosphere of nitrogen for 48 hours. The mixture is cooled, filtered through celite and then concentrated to dryness. The product is obtained by recrystallization from water and isopropanol.

EXAMPLE 15

Schenk Model

The compounds are evaluated for in vivo bone resorption inhibition and mineralization inhibition in an animal model system known in the field of bone metabolism as the Schenk Model. The general principles of this model system are disclosed in Shinoda et al., *Calcif. Tissue Int.*, 35, 87–99 (1983); and in Schenk et al., *Calcif. Tissue Res.* 11, 196–214 (1973), the disclosures of which are incorporated herein by reference.

Materials and Methods:

Animals

Preweaning 17-day-old (30 gms) male Sprague Dawley rats (Charles River Breeding Laboratories) are shipped with their mothers and placed in plastic cages with their mothers upon arrival. At 19 days of age, pups receiving Rat Chow and water ad libitum are randomly allocated into treatment or control groups comprising seven animals per group. On day 1 and again on day 7 all animals are given an intraperitoneal ("IP") injection of Calcein (1% solution in 0.9% saline solution; dosed at 0.2 ml/loo g body weight). On day 4 all animals are given an IP injection of tetracycline hydrochloride (1% solution in 0.9% saline solution; dosed at 0.2 ml/100 g body weight). These compounds label actively mineralizing bone and cartilage.

Dose Solutions and Dosing Procedure

All solutions are prepared for subcutaneous injection in 0.9% normal saline and adjusted to pH 7.4 using NAOH and/or HCl. Dose solution calculation is made by considering the mass of powder (based on molecular weight, hydration) of the active material in mg/kg (body weight) that corresponds to mgp/kg. Concentrations are based on dosing 0.2 ml/100 g body weight. Typically, all compounds are administered at 0.01, 0.1, 1.0 and 10.0 mg P/kg/day for 7 days. Compounds showing activity at 0.1 mg P/kg/day are then tested at logarithmic decrements down to 0.001 mg P/kg/day. Adjustments in dosage based on changes in body weight are made on a daily basis.

Necropsy, Tissue Processing and Histomorphometry

On day 8 after the start of dosing, all animals are sacrificed by IP overdose of pentabarbitol. Tibias are dissected free and placed in 70% ethyl alcohol. One tibia is dehydrated in graded ethanol solutions and embedded in methyl methacrylate as described in Schenk, *Methods of Calcified Tissue Preparation* (G. R. Dickson, Editor; Elsevier Science Publ., The Netherlands; 1984), the disclosures of which are incorporated herein by reference in their entirety. The tibia is sectioned longitudinally through the metaphyseal area. Specimens are stained on one surface with silver nitrate and mounted on microscope slides for evaluation with a Quantimet Image Analyzer (Cambridge Instruments, Inc.) using both incandescent and ultraviolet illumination. Metaphyseal trabecular bone content is measured in the region between the fluorescent label and the growth plate: expressed as percent of total area (bone+marrow). Epiphyseal growth plate width is obtained as the mean value of 10 equally-spaced measurements across the section.

Statistical evaluation of data is made using parametric and non-parametric analysis of variance and Wilcoxons rank sum test to determine a statistically significant effect compared to control animals. The Schenk model provides data for in vivo bone resorption inhibition by the compounds.

EXAMPLE 16

Adjuvant Arthritis Model

There are numerous animal models of arthritis, among these is adjuvant-induced arthritis using *Mycobacterium butyricum*. This model in a number of ways mimics rheumatoid arthritis in the human (joint swelling associated with cellular and pannus invasion of the joint space, bone resorption, and release of chemotaxic factors and lysosomal constituents into the joint space) (1,2). A number of prophylactic and therapeutic studies have indicated the potential use of anti-inflammatory drugs (3,4) and diphosphonates in arthritis (5,6).

REFERENCES

1. Pearson, C., Wood F. (1959), Studies of Polyarthritis and Other Lesions Induced by Injection of Mycobacterial Adjuvant. 1. General Clinical and Pathological Characteristics and Some Modifying Factors, *Arth. Rheum.*, 2:440–459.
2. Blackman, A., Burns, J. W., Framer, J. B., Radziwonik, H., Westwick, J. (1977), An X-ray Analysis of Adjuvant Arthritis in the Rat. The Effect of Prednisolone and Indomethacin, *Agents and Actions*, 7:145–151.

3. Winter, C. A., Nuss, G. W. (1966), Treatment of Adjuvant Arthritis in Rats with Anti-inflammatory Drugs, *Arth. Rheum.*, 9:394–404.
4. Winder, C. V., Lembke, L. A., Stephens, M. D. (1969), Comparative Bioassay of Drugs in Adjuvant-Induced Arthritis in Rats: Flufenamic Acid, Mefenamic Acid, and Phenylbutazone, *Arth. Rheum.*, 12:472–482.
5. Francis, M. D., Flora, L. King, W. R. (1972), The Effects of Disodium Ethane-1-Hydroxy-1-Diphosphonate on Adjuvant Induced Arthritis in Rats, *Calcif. Tiss. Res.*, 9:109–121.
6. Flora, L. (1979), Comparative Antiinflammatory and Bone Protective Effects of Two Diphosphonates in Adjuvant Arthritis, *Arth. Rheum*, 22:340–346.

Adjuvant arthritis is a severe cellulitis and synovitis induced in male rats (either Sprague Dawley or Lewis strain) by a single subcutaneous (SC) injection of Mycobacterium butyricum (8 mg/ml) in mineral oil on day 0. The compounds are dosed once daily either orally (PO) or parenterally (SC) and can be tested in either prophylactic (from day 0) or therapeutic (from day 9 or 10 or 14) protocols. Antiarthritic efficacy can be measured as a reduction in paw volume, body weight loss, bone loss or reactive new bone formation compared to the saline-treated arthritic controls. Treatment can be stopped and the "flare" response (rapid increase in inflammation) examined, which indicates a compound's ability to maintain efficacy.

Materials and Methods

A. Animals

Animals used are male Lewis rats (LEW). On arrival, the rats are randomized by computer generated random numbers and placed in individual wire suspended cages. Food and water are administered ad libitum, throughout the entire study. Routine care and maintenance of the animals are performed according to State and Federal regulations. Each rat is identified with a number placed in front of the cage and on the tail of the rat.

B. Experimental Design

On day 1 body weights (BW) and hind paw volume [(PV) recorded by a mercury displacement method using a pressure transducer linked into a computer] measurements are taken on all rats. On day 0, the induction of arthritis using MFA [*Mycobacterium butyricum* (Mb) 4.4 mg/kg in oil] is as follows: rats are anesthetized and receive a single SC injection of MFA at the base of the tail under aseptic conditions.

Paw volumes and body weights are measured thereafter on various days, usually twice a week. For the prophylactic protocol, rats are randomly allocated into groups of 8–10 rats and treatment begins on day 0 and continues daily until termination. For the therapeutic protocol, the rats are randomized into treatment groups of 8–10 rats according to their PV on day 10. Dosing begins on day 10 and continues daily until termination. For both protocols, animals are placed in shoe box cages with deep bedding on or before day 10.

Dosing Solutions

For Drugs Unlikely to Oxidize

Drugs are weighed out on a calibrated balance and then mixed with distilled water in a volumetric flask. The solution is adjusted to pH 7.4 with 0.1N NaOH. Then the solution is filtered through a 0.45 μm sterile filter into a sterile storage container. When not in use, the solution is stored in the refrigerator.

For Drugs Likely to Oxidize

Drugs are weighed out on a calibrated balance and then mixed with deoxygenated water in a volumetric flask. The stock solution is filtered through a 0.45 μm sterile filter into a sterile storage container. When not in use, the stock solution is kept refrigerated.

On a daily basis, a specific amount of solution is removed from the stock solution, put into small dosing beaker and then adjusted to pH 7.4 according to a predetermined calculation. Further dilutions of the adjusted solution can be made if necessary (with deoxygenated water).

Drug calculations are made based on the molecular weight, the purity of the compound, the amount based on mg/kg (body weight) and the desired final concentration in mgP/kg. The volume dosed per rat is 0.1 ml/100 gm of body weight subcutaneously, given as an injection in the inguinal fold of the animal, alternating sides each day or 1 ml/200 gm BW given orally using a curved stainless steel dosing tube. Adjustments based on changes in body weight are made weekly.

Radiographs, Necropsy and Tissue Collection

At termination, each rat is sacrificed with 1 ml Socomb® intraperitoneally (IP). Immediately a whole body radiograph is taken by a Torrox 120D x-ray unit at MA=5, ISUP=50 and time=60 sec. on Kodak non-screen medical film. Hind legs are removed from each rat and fixed in 10% buffered formalin along with a piece of liver, kidney, spleen, and thimus. The tibiotarsal joints are decalcified in 4% EDTA, pH 7.4 and processed routinely in paraffin blocks and H+E stain. The organ parts also processed in paraffin and stained H+E.

The histology sections are evaluated qualitatively for bone and soft tissue lesions using light microscopy. Radiographs are graded for bone resorption (BR) in 6 anatomical trabecular bone sites in each hind leg and 4 sites in each front leg on a scale of 0–3 giving an arbitrary score of 0–60 for all 4 legs. For reactive new bone formation (RNB), radiographs are graded on a severity scale of 0–3 for the lateral and medical surfaces of the tibia and then 0–2 for all other areas mentioned above, giving an arbitrary score of 0–44.

D. Statistical Analysis:

Data analysis on paw volume, bone resorption and reactive new bone formation is performed by student's t-test and one-way analysis of variance with Tukeys (SAS) (12). Differences are considered significant at p=0.05 or less.

This model provides in vivo data for the efficacy of antiarthritic compounds in terms of reducing paw swelling bone loss and reactive new bone formation compared to the saline treated arthritic animals.

EXAMPLE 17

Capsules are prepared having the following composition:

|  | Mg Per Capsule |
|---|---|
| Active Ingredient | |
| Cis-Octahydro-6,6-diphosphono-1,1-dimethyl-1-pyrindinium iodide salt | 350.0 |
| Excipients | |
| Lactose | 90.0 |
| Microcrystalline Cellulose | 60.0 |
| Magnesium Stearate | 1.0 |

The capsules having the above composition are prepared using conventional methods as described below:

The active ingredient is mixed with the microcrystalline cellulose in a turn shell blender for approximately ten (10) minutes.

The resulting mixture is passed through a hammer mill with an 80 mesh screen.

The mixture is put back into the twin shell blender along with the lactose and is then mixed for approximately fifteen (15) minutes.

The magnesium stearate is next added and blended for an additional five (5) minutes. The resulting blend is then compressed on a piston-activated capsule filler.

Any of the compounds prepared according to Examples 1 to 13 may be substituted for the active ingredient in the capsule prepared hereinabove.

EXAMPLE 18

Tablets are prepared having the following composition:

|  | Mg Per Tablet |
|---|---|
| Active Ingredient |  |
| Octahydro-4-amino-6,6-diphosphono-1,1-dimethyl-1-pyrindinium chloride | 700.00 |
| Excipients |  |
| Lactose (spray-dried) | 200.0 |
| Starch (1500) | 100.0 |
| Magnesium Stearate | 25.0 |

Tablets are prepared having the above composition using conventional methods as described below:

The active ingredient is ground in a ball mill for approximately thirty (30) minutes. The milled active ingredient is then blended in a twinblade mixer with the spray-dried lactose for approximately twenty (20) minutes.

The starch is added to the mixture and is then mixed for an additional fifteen (15) minutes. The blend is compressed into tablets on a standard tablet press.

Any of the compounds prepared according to Examples 1 to 13 may be substituted for the active ingredient in the tablet prepared hereinabove.

EXAMPLE 19

Injectable solutions are prepared by conventional methods using 10.0 ml of physiological saline solution and 7.0 mg P of cis-octahydro-6,6-diphosphono-1,1-dimethyl-1-pyrindinium salt, adjusted to pH =7.4.

One injection, one time daily for 4 days, results in appreciable alleviation of hypercalcemia of malignancy in patients weighing approximately 70 kilograms.

Any of the compounds prepared according to Examples 1–14 may be substituted for the active ingredient in the injection prepared hereinabove.

EXAMPLE 20

A Caucasian male, weighing approximately 92 kilograms, seventy-two years of age, suffering from moderate to severe pain, and occasional swelling, of the right knee. After approximately one year of steadily increasing discomfort, he visits a physician who renders a clinical diagnosis of osteoarthritis of the right knee, which was subsequently verified by X-ray diagnosis.

After a period of ameliorative therapy of various NSAIDs, including aspirin, naprosen, and ketoprofen, his symptoms continue to worsen and his condition appears to degenerate. He returns to his physician who then prescribes the tablets prepared as described in Example 18 twice daily two hours before or after meals for a period of three months. His clinical symptoms of pain and swelling, particularly with extended walking, improved significantly after his 3 months of therapy. At the conclusion of three months at a dosage of 2 tablets per day, the therapy is continued at one-half the dosage originally prescribed (i.e. 1 tablets per day) indefinitely.

EXAMPLE 21

A black female, weighing approximately 65 kilograms, fifty-five years of age, presents with swelling and deformation of the finger joints of both hands, with partial loss of strength and/or dexterity of her fingers and hands. Upon visual and X-ray examination and various appropriate clinical tests approved by the American Rheumatological Association (ARA) she is diagnosed with rheumatoid arthritis.

After an unsuccessful analgesic and anti-inflammatory therapy, her physician prescribes the tablets prepared in Example 18, two times daily two hours before or after meals for a period of four months. After a month of therapy, her symptoms of knuckle swelling noticeably improves and her range of finger motion increases significantly; she continues therapy for the remainder of the four months, after which her physician continues the prescribed dose for an additional two months.

EXAMPLE 22

A female of Hispanic origin, twelve years of age, weighing approximately 37 kilograms, presents to the physician with idiopathic juvenile rheumatoid arthritis. Her symptoms include marked inflammation of multiple joints, complicated by heat and tenderness and indicating rapid and pathological degeneration of joint function.

Her physician refers her to a rheumatologist who immediately prescribes aggressive therapy by IV administration of the solution prepared as described in Example 19 over a period of three days, at the rate of 1 injection per day, administered over two hours. At the conclusion of the IV regimen, the physician prescribes the tablets prepared as described in Example 18, for a period of two months, during which she exhibits marked improvement with increased mobility and decreased pain. For the succeeding two months, the physician reduces her dose to ¾ of the original oral dose by prescribing 3 tablets over a period of two days, i.e. one 2-tablet day alternating with one 1-tablet day. At the conclusion of this regimen the dosage is again reduced to ¼ of the original dose by giving her the tablets prepared as described in Example 18, 1 tablet every day for an additional four months.

EXAMPLE 23

A 60-year-old Caucasian female weighing 62 kg, experiences severe back pain. Her physician, with the aid of a radiologist diagnoses her as having a crush fracture of the L1 vertebrae presumably due to osteoporotic bone loss. The patient is prescribed a three month, once-daily dosage regimen of a 700 mg tablet prepared accordinging to the procedure described in Example 18. The 700 mg tablet is taken either two hours before or two hours after any given meal. After three months, the dosage is reduced to a 350 mg capsule, prepared as described in Example 17, taken every other day for a period of three months. Her physician then puts her on a maintenance dosing regimen wherein she takes a 100 mg capsule every day for six months. After six months on the maintenance dosing regimen the patient is not experiencing any further back pain. Follow-up x-rays reveal no additional fractures.

EXAMPLE 24

A 75-year-old Oriental female weighing 53 kg suffers a fractured hip after a fall. She is hospitalized and diagnosed as having osteoporosis. A treatment regimen of calcitonin injections is prescribed. The calcitonin injections are painful to the patient and she is unable to comply with the calcitonin regimen. Her physician then switches her therapy to an oral phosphonate regimen. She is administered a 700 mg tablet prepared according to the procedure described in Example 18, twice daily for one month. At the end of this one month of therapy, she is given a 700 mg tablet, once daily for two months. At the end of this two month period, she is given a 100 mg capsule, prepared according to the procedure described in Example 17, daily for three months. A follow-up visit to her physician reveals no apparent decrease in mineral density of the forearm as determined by photonabsorptimetry.

EXAMPLE 25

A 85-year-old Native American male weighing 65 kg presents to his physician with severe back pain. X-rays reveal multiple minor vertebral body collapse resulting from significant bone loss due to osteoporosis. The patient is prescribed a two month regimen of a 700 mg tablet and a 350 mg capsule to be taken on the same day, eight hours apart, prepared according to the procedures described in Examples 18 and 17, respectively. After two months on this regimen, his dosage is reduced to 350 mg tablet once a day for two months. X-rays are taken and an additional crush fracture is noted. He is then put on a maintenance regimen of a 100 mg capsule, prepared according to the procedure described in Example 17, once a day for six months. At the end of this six months, no significant apparent decrease in bone density is observed.

What is claimed is:

1. A quaternary nitrogen-containing, cyclic ring-containing phosphonate compound and the pharmaceutically-acceptable salts and esters thereof, having the following structure:

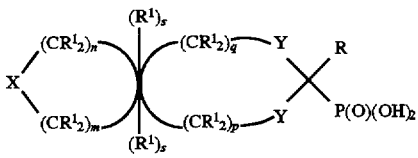

wherein (a) each X and Y are independently selected from nil, O, S, $NR^1$ and $N^+(R^2)_2$; if no $R^1$ is $N^+(R^2)_3$, then at least one of X or Y must be $N^+(R^2)_2$;

(b) m and n and m+n are integers from 0 to 5, p and q and p+q are integers from 0 to 3;

(c) s is an integer from 0 to 2 and when m+n=0 and X is nil, s=2;

(d) each $R^1$ is independently selected from the group consisting of nil, $N^+(R^2)_3$, $R^9SR^6$, $SR^6$, hydrogen, hydroxy; unsubstituted or substituted $C_1$–$C_8$ alkyl, —$OR^3$, —$CO_2R^3$, —$O_2CR^3$, $NR^3_2$, —$N(R^3)C(O)R^3$, —$C(O)N(R^3)_2$, halogen, —$C(O)R^3$, arylalkyl, nitro, unsubstituted or substituted aryl, and combinations thereof, (e) each $R^2$ is independently selected from the group consisting of nil; substituted or unsubstituted $C_1$–$C_{35}$ alkyl, substituted or unsubstituted phenyl, benzyl, or $R^9SR^6$;

(f) each $R^3$ is independently selected from the group consisting of hydrogen, substituted or unsubstituted $C_1$–$C_8$ alkyl, and $R^9SR^6$;

(g) each $R^6$ is independently selected from the group consisting of H, —$C(O)R^7$, $C(O)OR^7$, $C(S)OR^7$, $C(S)R^7$, $C(O)NR^7_2$, and $C(S)NR^7_2$, wherein $R^7$ is hydrogen, or substituted or unsubstituted $C_1$–$C_8$ alkyl;

(h) R is $PO_3H_2$ or $P(O)(OH)R_4$, wherein $R_4$ is substituted or unsubstituted $C_1$–$C_8$ alkyl; and (i) $R^9$ is substituted or unsubstituted C1–C8 alkyl, (j) wherein each ring has from to 4 to 7 members.

2. A compound according to claim 1 wherein m+n equals 3.

3. A compound according to claim 1 wherein m+n equals 2.

4. A compound according to claim 1 wherein Y is nil and q+p equals 2.

5. A compound according to claim 2 wherein q+p equals 3.

6. A compound according to claim 2 wherein Y is a nitrogen and q+p equals 1.

7. A compound according to claim 6 wherein q+p equals 2.

8. A compound according to claim 2 wherein $R^1$ is $N^+(R^2)_3$; $SR^6$; $R^9SR^6$; hydrogen; unsubstituted or substituted $C_1$–$C_8$ alkyl; $CO_2R^3$; —$O_2CR^3$; —$NR^3_2$; —$N(R^3)C(O)R^3$; —$OR^3$; or —$C(O)N(R^3)_2$.

9. A compound according to claim 8 wherein $R^1$ is $N^+(R^2)_3$; $SR^6$; $R^9SR^6$; hydrogen; $CO_2R^3$; —$OR^3$; or —$NR^3_2$.

10. A compound according to claim 9 wherein $R^1$ is $N^+(R^2)_3$; $SR^6$; $R^9SR^6$ or $CO_2R^3$.

11. A compound according to claim 9 wherein $R^1$ is $CO_2R^3$; —$OR^3$; or $NR^3_2$ and $R^3$ is $R^9SR^6$.

12. A compound according to claim 2 wherein $R^2$ is substituted or unsubstituted $C_1$–$C_{35}$ alkyl; phenyl; benzyl or $R^9SR^6$.

13. A compound according to claim 11 wherein $R^6$ is H; —$C(O)R^7$; —$C(S)R^7$; or $C(O)N(R^7)_2$.

14. A compound according to claim 12 wherein $R^6$ is H; —$C(O)R^7$; —$C(S)R^7$; or $C(O)N(R^7)_2$.

15. A compound according to claim 1 wherein X is nil and $R^1$ is $N^+(R^2)_3$.

16. A compound according to claim 1 wherein at least one Y is nil and $R^1$ is $N^+(R^2)_3$.

17. A pharmaceutical composition comprising:
(a) a safe and effective amount of a quaternary nitrogen containing cycloalkane phosphonate compound according to claim 1; and
(b) pharmaceutically-acceptable excipients.

18. A pharmaceutical composition comprising:
(a) a safe and effective amount of a quaternary nitrogen containing cycloalkane phosphonate compound according to claim 4; and
(b) pharmaceutically-acceptable excipients.

19. A pharmaceutical composition comprising:
(a) a safe and effective amount of a quaternary nitrogen containing cycloalkane phosphonate compound according to claim 5; and
(b) pharmaceutically-acceptable excipients.

20. A pharmaceutical composition comprising:
(a) a safe and effective amount of a quaternary nitrogen containing cycloalkane phosphonate compound according to claim 15; and
(b) pharmaceutically-acceptable excipients.

21. A pharmaceutical composition comprising:
(a) a safe and effective amount of a quaternary nitrogen containing cycloalkane phosphonate compound according to claim 16; and
(b) pharmaceutically-acceptable excipients.

22. A method for treating or preventing pathological conditions associated with abnormal calcium and phosphate metabolism in humans or other mammals in need of such treatment, comprising administering to a human or other mammal a safe and effective amount of a quaternary nitrogen containing cyclic ring-containing phosphonate compound of claim 1.

* * * * *